United States Patent [19]

McCall

[11] 4,419,188

[45] Dec. 6, 1983

[54] THERMALLY COUPLED EXTRACTIVE DISTILLATION PROCESS

[76] Inventor: Thomas F. McCall, 5425 Windsor La., Fairway, Kans. 66205

[21] Appl. No.: 350,592

[22] Filed: Feb. 22, 1982

Related U.S. Application Data

[63] Continuation of Ser. No. 155,660, Jun. 2, 1980, abandoned.

[51] Int. Cl.³ ............................................. B01D 3/40
[52] U.S. Cl. ...................................... 203/24; 203/57; 203/84; 203/98
[58] Field of Search ...................... 203/24, 26, 57, 58, 203/59, 60, 27, 61–70, 21–23, 25, 71, 75, 78, 74, 82, 84, 93, 94, 98, DIG. 4; 585/800, 810, 833, 860, 862, 864, 865, 901; 208/325–327, 330–333, 354, 355, 357, 358; 62/26, 27, 30; 196/100, 105, 106, 111

[56] References Cited

U.S. PATENT DOCUMENTS

| | | | |
|---|---|---|---|
| 3,705,204 | 12/1972 | Horie et al. | 585/810 |
| 3,729,944 | 5/1973 | Kelley et al. | 62/26 |
| 3,788,954 | 1/1974 | Cantrell | 203/74 |
| 4,025,398 | 5/1977 | Haselden | 203/98 |
| 4,246,073 | 1/1981 | Umeda et al. | 203/27 |

Primary Examiner—Frank Sever
Attorney, Agent, or Firm—Thomas M. Scofield

[57] ABSTRACT

Thermally coupled extractive distillation; a feed stock (for example, a C4 or C5 cut from an ethylene plant) is distilled by thermally coupled extractive distillation to remove paraffins and mono-olefins as a raffinate stream, as well as acetylenic hydrocarbons in a separate steam, thus segregating the C4 or C5 diolefin, the process using extraction solvents such as acetonitrile (ACN), dimethyl formamide (DMF), furfural, acetone, dimethylacetamide or N-methyl-2-pyrrolidone mixed with 0–12 weight percent of water, a bottoms stream of virtually acetylene free solvent further being produced; thermally coupled extractive distillation utilizing one to three coupled vessels to produce at least two and preferably three discrete, different volatility streams therefrom, as well as an extractive solvent recycle stream.

25 Claims, 10 Drawing Figures

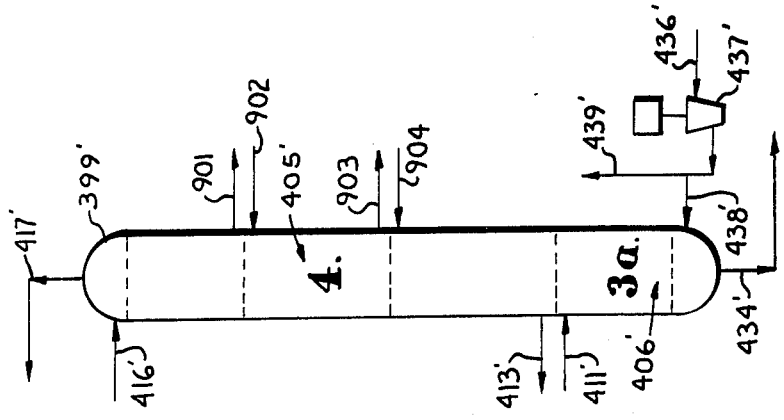
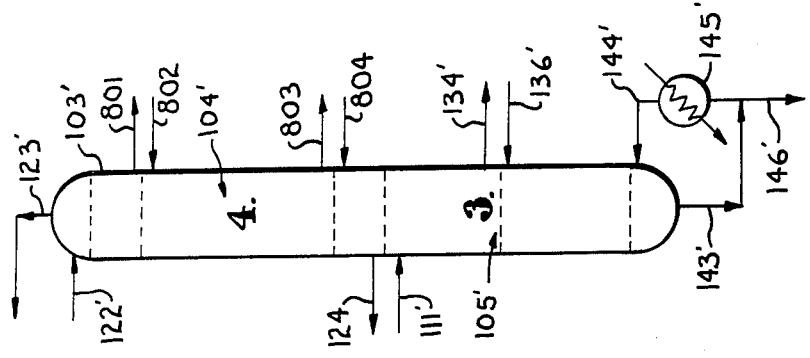
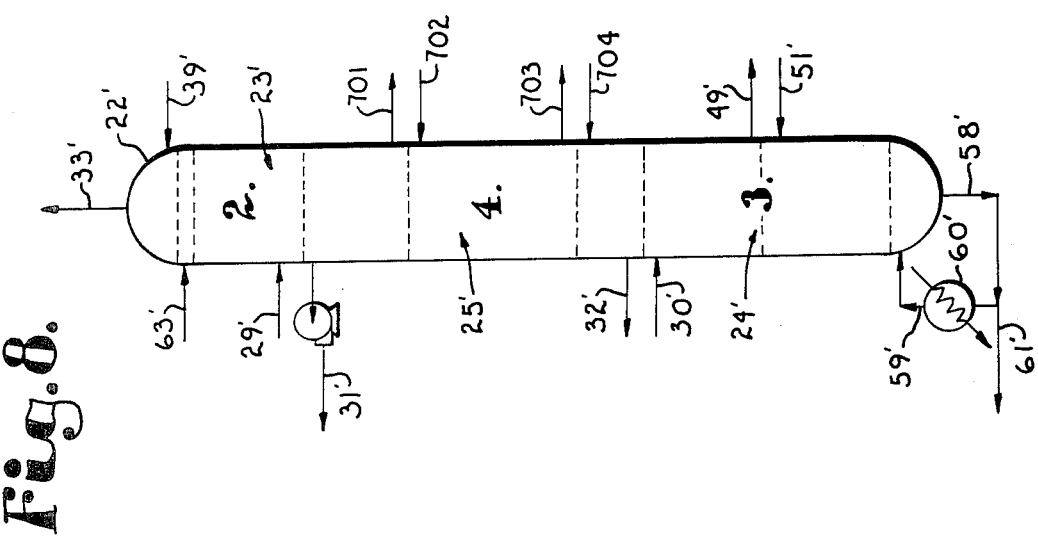

THERMALLY COUPLED EXTRACTIVE DISTILLATION PROCESS

CONTINUING DATA

This is a continuation of application Ser. No. 6/155,660, filed 6/0280, now abandoned.

BACKGROUND OF THE INVENTION

One field of this invention is the purification and recovery of diolefins, in particular C4 and C5 olefins such as butadiene and isoprene.

In the manufacture of ethylene and/or propylene by thermal cracking of naphtha, LPG, gas, oil, or fractions thereof, a hydrocarbon fraction containing conjugated diolefins may be obtained. From this fraction may be recovered a C4 fraction comprising 1,3 butadiene, n-butanes, n-butenes, isobutene, vinylacetylene, ethyl acetylene, 1,2-butadiene, and other C4's. A C5 fraction comprising isoprene, 1,3-pentadeine, cyclopentadeine, paraffinic compounds (e.g. isopentane and n-pentane) olefins (e.g. 2-methyl butene-1 and pentene-1), acetylenes (e.g. pentyne-1 and 1-pentene-4-yne), and other hydrocarbons (e.g. benzene, hexane, cyclopentane, cyclopentene and dicyclopentadiene) may also be recovered.

In diolefin purification, removal of acetylenic hydrocarbons is of particular importance. Diolefins such as 1,3 butadiene and isoprene are monomer raw materials for the production of synethetic rubber by catalytic solution polymerization. Acetylenes such as 2-methyl-1-butene-3-yne, inhibit the desired polymerization to reaction in concentrations of small as 300 ppm (parts per million). They react with polymerization catalysts, increasing catalyst consumption. For most solution polymerization work, acetylenes should be limited to 100 to 400 ppm maximum concentration, preferably less than 100 ppm.

Background information with respect to the subject process may be found in:

(1) "Techniques of Organic Chemistry" Volume 4, "Distillation", Second Edition, Interscience, particularly Chapter IV "Extractive and Azetotropic Distillation" by Carl S. Carlson and Joseph Stewart, Esso Research and Engineering Company, Linden, New Jersey and references noted thereafter.

(2) Chemical Engineering Progress, Volume 68, No. 10, October 1972 "Thermally Coupled Distillation - A Case History", W. J. Stupin, et al.

(3) Cahn, et al. U.S. Pat. No. 3,058,893 "Separation of Multicomponent Mixture In Single Tower", issued Oct. 16, 1962.

(4) August, 1969 Petro/Chem Engineer article by Dr. Thomas Reis "Compare Butadiene Recovery Methods (Processes, Solvents, Economics)."

(5) U.S. Pat. No. 4,134,795, issued Jan. 16, 1979 "Acetylenes Removable From Diolefin Streams By Extractive Distillation", inventor Colin S. Howat III. This patent contains an extensive listing of patents, as well as characterization thereof, related to extractive distillation.

While the subject improvements are particularly adaptable to the purification and recovery of diolefins, as previously mentioned, there are numerous other extractive distillation systems where the subject improvements and inventions may be applied. Without limitation, then, the following components to be separated and the solvent with which such would be extractively distilled are given: (1) Ethanol and water with solvent glycerol, (2) Acetone and methanol with water, (3) Propane and propylene with acrylonitrile, (4) Aromatic hydrocarbons and non-aromatic hydrocarbons with phenol, (5) Heptane and methylcyclohexane with aniline, (6) Benzene and cyclohexane with aniline, (7) Acetic acid and water with high boiling hydrocarbons.

It might be noted that the just listed systems have two primary components for separation and, thus, differ from the C4 and C5 hydrocarbon separation which would involve an overhead rafinate stream, a diolefin stream and an acetylene stream or the equivalent. The subject system, that is, is particularly adaptable to separation of two primary components or three. More cuts may be taken under special circumstances.

The subject of the present invention is a thermally coupled extractive distillation process which most effectively and efficiently carries out the conventional goals of the distillation systems above mentioned and those related thereto.

SUMMARY OF THE INVENTION

The present invention may be summarized as a process for the separation of at least two material substances whose relative volatility approaches unity at some point in an ordinary distillation, thus requiring use of an extractive solvent to change relative volatilities, as follows:

(1) Extractively distilling, in a first distillation zone, a feed stream containing higher and lower boiling components, in the presence of extractive solvent, thereby to separate a relatively high volatility overhead vapor stream and a relatively low volatility liquid bottoms stream;

(2) Supplying said overhead stream to the lower portion of a second distillation zone and the bottoms stream to the upper portion of a third distillation zone;

(3) Passing overhead vapo streams from the third distillation zone to a lower level of a fourth distillation zone and a lower level of the first distillation zone;

(4) Passing a feed stream of predominantly extractive solvent to an upper part of the second distillation zone;

(5) Passing a liquid stream from the lower portion of the second distillation zone to an upper level of the first distillation zone and also to an upper level of the fourth distillation zone;

(6) Passing a liquid stream from the lower portion of the fourth distillation zone to an upper portion of the third distillation zone;

(7) Carrying out extractive distillations in the second, third and fourth distillation zones (also in the presence of said extractive solvent);

(8) Withdrawing an overhead and highest volatility vapor stream from the top of the second distillation zone;

(9) Withdrawing an intermediate, next lower volatility stream, including some extractive solvent, from the fourth distillation zone intermediate the ends thereof;

(10) Optionally (but preferably) withdrawing an intermediate, third lower volatility stream, including some extractive solvent, from the third distillation zone intermediate the ends thereof;

(11) Withdrawing a lowest volatility liquid bottoms stream, predominantly comprising extractive solvent, from said third distillation zone;

(12) Passing at least a portion of the overhead withdrawal stream from the second zone and intermediate withdrawal streams from the fourth and third zone (if a withdrawal stream is taken from the third zone) out of the system;

(13) Condensing the second distillation zone overhead vapor stream and recycling at least a portion thereof as reflux to an upper level of said second distillation zone,

(14) Recycling at least a portion of the third zone bottoms withdrawal stream to an upper level of the second zone as the major portion of the feed stream thereto.

Optionally, but preferably, a portion of the third distillation zone bottoms stream is recycled to join the feed stream to the first zone.

Further optionally but preferably, a portion of the solvent from the fourth distillation zone withdrawal stream (and also from the third distillation zone withdrawal stream if present) is separated and recycled to intermediate levels of the fourth zone and third zone, respectively.

Optionally, but preferably, a portion of the third zone liquid bottoms are partially vaporized and used as the primary heat source to accomplish the distillation of the four zones.

The overhead vapor stream from the second zone may be compressed before condensing same. The overhead vapor stream from the third distillation zone may be compressed before passing same to the fourth and first zones.

OBJECTS OF THE INVENTION

A first and primary object of the invention is to provide a thermally coupled extractive distillation system which is energy and apparatus efficient.

Another object of the invention is to provide various particular embodiments of thermally coupled extractive distillation systems which accomplish particular distillation goals, as well as energy and apparatus efficiency.

Another object of the invention is to provide such thermally coupled extractive distillation systems wherein the solvent used in the system is maximally protected from degradation due to excessive reboiler heat.

Another object of the invention is to provide such thermally coupled extractive distillation systems wherein fouling of equipment, particularly trays and reboilers, due to polymerization of such compounds as diolefins is minimized.

Other and further objects of the invention will appear in the course of the following description thereof.

THE DRAWINGS

In the drawings, which form a part of the instant specification and are to be read in conjunction therewith, embodiments of the invention are shown as exemplified in schematic flow diagrams which are diagrammatic representations of the process of the present invention. Each flow diagram represents an exemplary embodiment and the process itself is not limited to the specific arrangements shown.

It should be particularly noted that the drawing figures and symbols represent chemical unit operations and conventional ancillary equipment, such as spare pumps, valves, level controls and the like have not been illustrated for clarity. Additionally, secondary process streams (e.g. vent lines) and utility streams have been omitted.

BRIEF DESCRIPTION OF DRAWINGS

FIG. 7 shows a variation in the apparatus and process of FIG. 5 as applied to the distillation zone or column 3a of that view. Accordingly, FIG. 7 only shows the bottom of the distillation column 3a and the different associated apparatus therewith, the other portion of the system of FIG. 7 being identical with the center and right hand showing of FIG. 5.

FIG. 8 is a fragmentary showing of a distillation vessel adapted to replace the distillation vessel of FIG. 1 having distillation zones 2, 3 and 4 therein. Otherwise, the system of FIG. 8 is the same as seen in FIG. 1.

FIG. 9 is a fragmentary view showing a distillation vessel adapted to replace the distillation vessel having distillation zones 3 and 4 therein of FIG. 2.

FIG. 10 is a fragmentary showing of a substitute distillation vessel to be inserted in FIG. 5, optionally, as a replacement for the distillation vessel therein containing distillation zones 3a and 4.

GENERAL CONSIDERATIONS

Figure 1:
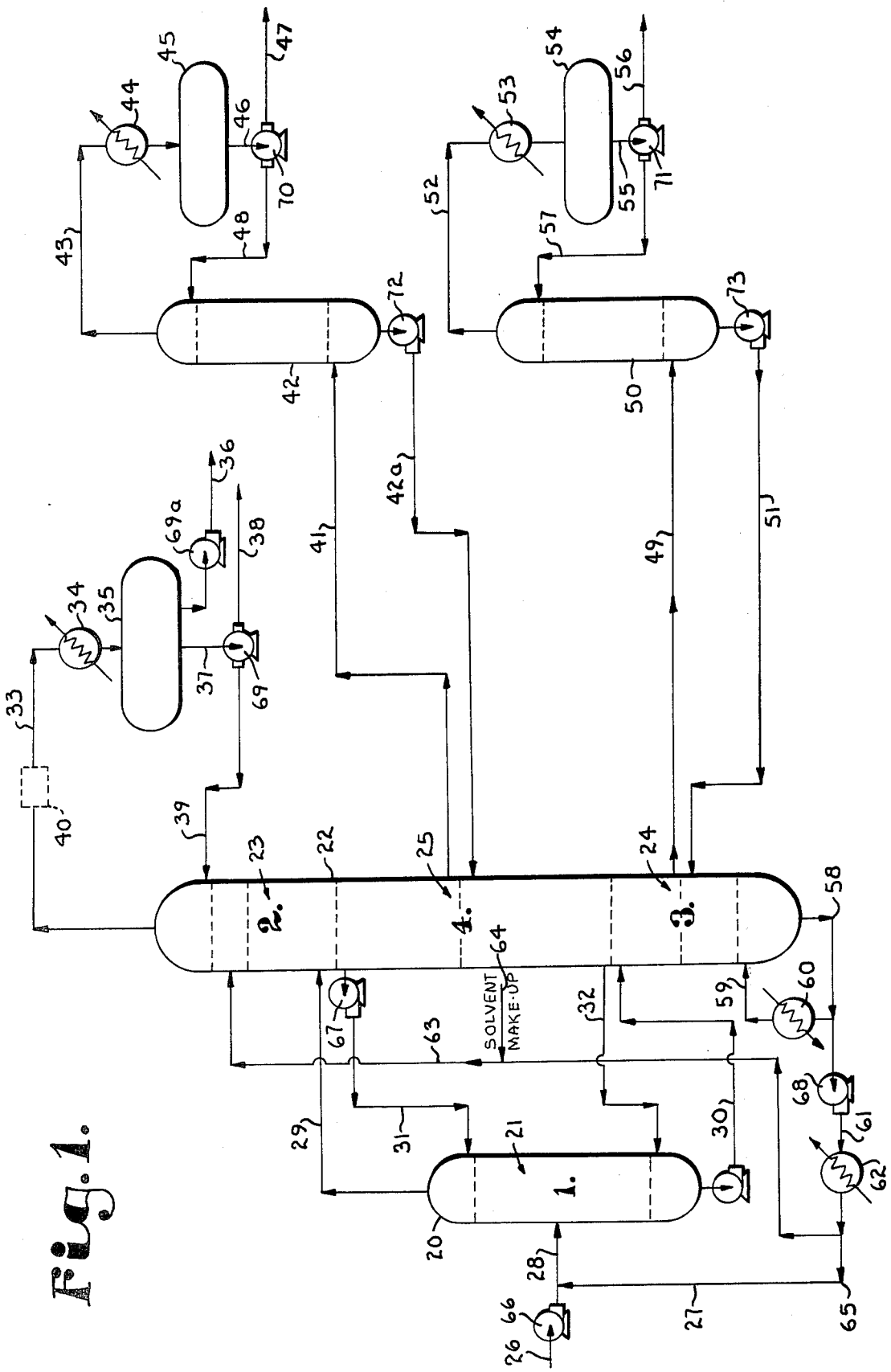
FIG. 1 shows a first arrangement of the subject thermally coupled extractive distillation system wherein the first distillation zone is in a first tower and the second, third and fourth distillation zones are in a second tower, with the second zone in the top of the second tower, the third zone at the bottom of the second tower and the fourth zone therebetween in the second tower.

Typical hydrocarbon fractions used as feed in diolefin separation processes contain hydrocarbons which are lighter or more volatile than the desired hydrocarbons and some which are heavier or less volatile than the desired hydrocarbons. One or more distillation steps prior to the processes described in this application may be conveniently performed on the crude feed to remove these heavy and light ends of the crude feed stream. U.S. Pat. Nos. 3,851,010 and 3,317,626 describe such operation as being accomplished in a single distillation column. Heavy ends removal is also shown in U.S. Pat. Nos. 2,459,403; 2,426,705 and 2,407,997.

With respect to the illustrated flow diagrams and described processes, at least four distillation zones, variously located in distillation towers, are identified. Certain feed streams thereto, including the substances to be separated, mixed such feeds with solvent, and solvent, per se, are shown flowed into certain positions in the zones. This is also true with respect to the external feeds between zones and parts thereof in different vessels. Yet further, the positions of the withdrawal streams, recycle hydrocarbon reflux and solvent return lines are also specifically described with respect to zone position. For further specification, the following data is given with respect to the subject thermally coupled extractive distillation system applied to 1,3 butadiene extraction from a C4 hydrocarbon cut. Technical information relative to solvent concentrations, vapor/liquid ratios and numbers of trays, as well as line locations relative to tray position is provided as follows:

(1) Distillation zone 1 has 77 trays therein. (Other distillation apparatus such as packing can be used, taking into account the assumption that there is a 70 percent tray efficiency for the case of distilling trays.) The mol ratio of hydrocarbon vapor to hydrocarbon liquid at the top of the zone is in the range of 2.2 to 1. The liquid phase is approximately 80 mol percent solvent, 20 mol percent hydrocarbon throughout the zone. The feed to zone 1 is located on the 57th tray from the top zone 1.

(2) Zone 2 has 42 trays. The solvent feed is located at the tenth tray from the top of zone 2. Mol ratio of the hydrocarbon vapor to hydrocarbon liquid at the top of the zone is in the range of 1.3 to 1. Below the solvent feed point, the liquid phase is approximately 80 mol percent solvent and 20 mol percent hydrocarbon throughout the zone. In the zone above the solvent feed input at tray 10, most of the solvent is removed from the rising vapors.

(3) The third zone, which serves to strip the hydrocarbon from the solvent, has 45 trays. The mol ratio of solvent to hydrocarbon in the liquid phase at the bottom of this zone approaches 100,000. The ratio of solvent vapor flow to solvent liquid flow on the bottom tray is in the range of 0.21 to 1. The acetylene draw-off point is located at the 35th tray from the top of zone 3.

(4) Zone 4 has 77 trays. Mol ratio of hydrocarbon vapor to hydrocarbon liquid at the top of the zone is in the range of 0.9 to 1. The third phase is approximately 80 mol percent solvent and 20 mol percent hydrocarbon throughout the zone. The 1-3 butadiene draw-off point is located at the 57th tray from the top zone 4. (5) Tower 42 typically has 15 trays and operates with a reflux ratio of 0.2 to 1.

The above information with respect to the processing of a C4 cut to recover 1,3 butadiene applies to all of the flow systems seen in the various views when such specific process is carried out therein.

When a compressor is used, either on the overhead from the second or third zone, the purpose is to allow the overhead vapor from the second zone to be condensed using plant cooling water (typically 32° C.) as the cooling medium while maintaining a temperature at the bottom of zone 3 which is less than about 215° F. (101.7°) to minimize the problems of system fouling and solvent degredation.

The latter remarks on compressor use apply to C4 and C5 thermally coupled extractive distillation systems and, additionally to any systems where fouling and/or solvent degradation would result from higher temperature operation. Such compressor presence may also improve the energy balance by minimizing the sensible heat required to raise the solvent temperature.

FIG. 1

Referring to FIG. 1, therein is shown a first form of the subject thermally coupled extractive distillation process, carried out in a particular apparatus arrangement. A first distillation vessel 20 has a first distillation zone generally designated 21 therein. A second distillation vessel 22 has a second distillation zone 23 in the upper portion thereof, a third distillation zone 24 in the lower portion thereof and a fourth distillation zone 25 substantially centrally thereof.

Referring back to first distillation vessel 20, basic feed line 26 is joined by optional solvent recycle line 27, the common line thereafter 28 transmitting the basic multicomponent feed and optional solvent recycle substantially centrally of first distillation zone 21. Overhead vapor line 29 passes to the lower portion of the second distillation zone 23 in vessel 22 and liquid bottoms line 30 passes from the bottom of vessel 20 and distillation zone 21 to the upper portion of the third distillation zone 24. A liquid transmitting line 31 passes from the lower portion of second distillation zone 23 to an upper level of first distillation zone 21. Vapor line 32 passes from the upper portion of third distillation zone 24 to a lower level of first distillation zone 21.

Overhead vapor line 33 from the top of the vessel 22 and second distillation zone 23 has condenser 34 thereon before passing to receiver vessel 35. Water withdrawal line 36 is taken off vessel 35 from the bottom thereof. Material withdrawal line 37 splits into output line 38 and recycle line 39 back to the top of vessel 22 and second distillation zone 23. Optional compressor 40 may be employed on line 33 before condenser 34.

Intermediate next lower volatility withdrawal line 41, typically vapor, passes to rectifier tower 42. Bottoms solvent recycle line 42a returns to vessel 22 intermediate the ends of fourth distillation zone 25 substantially at the same level from which intermediate volatility lower withdrawal line 41 was taken. Overhead line 43 from the tower 42 passes, after condensing at 44, to accumulator or receiver 45. Line 46, from the bottom thereof, splits into withdrawal line 47 to go out of the system illustrated in the figure and return line 48 to the upper portion of tower 42. Lines 41 and 42a exit from and return to a lower portion of zone 25.

Optional, but preferred, intermediate, third lower volatility withdrawal line 49 passes to rectifier tower 50 from vessel 22 intermediate the ends of third distillation zone 24. Solvent recycle line 51 from the bottom of tower 50 returns to vessel 22 and third distillation zone 24 closely adjacent the withdrawal line 49. Overhead line 52 from tower 50, after condensation at 53, passes to accumulation at vessel 54. Bottoms line 55 from vessel 54 splits into out system line 56 and return line 57 to the top of tower 50.

From the bottom of vessel 22 and out of the bottom of third distillation zone 24 goes solvent recycle line 58. This splits into reboiler return line 59 having heater 60 thereon and solvent recycle line 61 with cooler 62 thereon. After cooler 62, line 61 becomes main solvent return line 63 to the top of vessel 22, as well as upper part of distillation zone 23. Makeup solvent line 64 joins line 63 intermediate its ends. Optional, but preferred solvent return line 65 becomes line 27 joining feed line 1 into vessel 20 and first distillation zone 21.

Pumps 66–73 inclusive are employed on lines 26, 31, 61, 37, 46, 55, 42a and 51, respectively.

The process as carried out in the apparatus system just described and defined in terms of distillation zones 1–4, inclusive in vessels 20 and 22, as well as the associate vessels and lines thereto may be described as follows:

(1) A feed stream 26 containing higher and lower boiling components is extractively distilled in a first distillation column or 21 in the presence of extractive solvent (lines 27, 31 and 32) to separate a relatively high volatility overhead vapor stream 29 and a relatively low volatility liquid bottoms stream 30.

(2) The overhead stream 29 is supplied to the lower end of a second distillation column or zone 23, while the bottoms stream 30 is supplied to the upper end or portion of a third distillation column or zone 24.

(3) Overhead vapor streams from the third distillation column or zone 24 are passed to a lower level of the first distillation column by line 32 and internally of vessel 22 to a lower level of fourth distillation column or zone 25.

(4) A second feed stream of predominantly extractive solvent is passed via line 63 (with makeup solvent as required in line 64) to an upper part of the second distillation column or zone 23 in vessel 22.

(5) Liquid streams are passed from the lower portion of the second distillation column or zone 23 to an upper level of the first distillation column or zone 21 via line 31 and also internally of vessel 22 to an upper level of fourth distillation column or zone 25.

(6) Internally of vessel 22, a liquid stream is passed from the lower portion of fourth distillation column or zone 25 to an upper portion of third distillation column or zone 24.

(7) Extractive distillations are carried out in the second, third and fourth distillation columns or zones 23, 24 and 25 in vessel 22, also in the presence of said extractive solvent via line 63.

(8) An overhead highest volatility vapor stream is withdrawn from the top of vessel 22 and the second distillation zone 23 via line 33. This vapor stream is optionally compressed at 40, condensed at 34 and passed into the receiver or accumulator vessel 35. A predominantly water withdrawal stream with some extractive solvent is taken off through line 36. The condensed bottoms from vessel 35 are passed therefrom via line 37 with line 39 recycling a portion of the overhead vapor stream as reflux to an upper level of the vessel 22 and second distillation column or zone 23. Line 38 passes a portion of the overhead withdrawal stream from the second distillation zone out of the system.

(9) An intermediate, next lower volatility stream, line 41 including a significant portion of extractive solvent, is withdrawn from vessel 22 and fourth distillation zone 25, intermediate the ends thereof and passed to rectifier tower 42, close to the bottom thereof. Overhead from tower 42, in line 43, is condensed at 44 and accumulated in vessel 45. Bottoms from vessel 44 through line 46 are split into reflux line 48 to the top of tower 42 and line 47 going out of the system illustrated. Recycle bottoms line 42a from tower 42 returns solvent and next lower volatility withdrawal materials from line 41 back to distillation zone 25 intermediate the ends thereof.

(10) An intermediate, third lower volatility stream, including some extractive solvent, is withdrawn (optionally, but preferably) through line 49 from the third distillation zone or zone 24 intermediate the ends thereof and passed to rectifier tower 50. Bottom return or recycle line 51 from vessel 50 back to vessel 22 intermediate the ends of third distillation zone 24 carries solvent and some third lower volatility withdrawal stream materials therein. Overhead line 52 from tower 50 is condensed at 53 and passed to accumulator 54. The bottoms line 55 from accumulator 54 splits into withdrawal line 56 and reflux return line 57 to the top of tower 50. Line 56 carries third lower volatility stream materials out of the system illustrated.

(11) A lower volatility liquid bottoms stream, predominantly comprising extractive solvent, is withdrawn from the bottom of vessel 22 via line 58, from the bottom of third distillation zone 24. At least a portion of the bottoms withdrawal stream in line 58 is recycled via line 63 to an upper lower level of the second distillation zone 23 as the major portion of the feed stream thereto. Optionally, a portion of the third zone bottoms stream joins the feed stream 26 to the first distillation zone 21 at 27 via line 65.

The above given generalized process description also applies to the processes as carried out in FIGS. 2–5, inclusive as well. The zones of distillation may be in different vessel arrangements with different flows internal rather than external and vice versa.

In a specific embodiment of the process in question, the feed in line 26 is a crude C4 feed having a composition (typical but not limiting) of 44 weight percent 1,3 butadiene, 23 percent isobutene, 12 percent butene-1,6 percent T-Butene-2,5 percent C-Butene-2, 4 percent N-Butene, 1.1 percent isobutane and lesser quantities of vinylacetylene, propyne, 1,2 butadiene and butyne-1, as well as propadiene. The optional solvent to feed line 27 could contain 90 percent ACN solvent (acetonitrile) and 10 percent water. The feed in line 28 to vessel 20 and first distillation zone 21 would be 64 percent solvent, 13 percent 1,3 butadiene, 7 percent water, 6 percent isobutene, etc. The latter assumes that the pound per hour rate of feed of the crude C4 feed is slightly more than one third the rate of solvent recycled into the feed. Percentages given are weight percents in all cases. A mol ratio of a solvent plus water to the hydrocarbon feed of four to one is preferable. The noted weight percentages correspond to this.

The overhead withdrawal line 33 flow from vessel 22 at the top of second distillation zone 23 typically might comprise 42 percent isobutane, 22 percent butene-1, 12 percent T-butene-2, 9 percent C-butene-2, 8 percent normal butene, 2 percent isobutane and 1 percent 1,3 butadiene. The hydrocarbon withdrawal stream 38 from the system would be approximately the same composition as in line 33 but, typically, about one quarter of the amount. The reflux flow in line 39 is approximately the same composition as line 33 and comprises the balance of the stream in line 33 less that taken out line 38. The composition of line 36 is 30 percent water and 20 percent solvent in a relativley low volume withdrawal stream.

The intermediate withdrawal line 41 from the fourth distillation zone 25 typically would have a composition of 91 percent 1,3 butadiene, 6 percent solvent and less than 1 percent water, propyne and C-butene-2. 1,2 butaliene would typically be less than two-tenths of a weight percent. The solvent return line 42a from tower 42 typically would carry a composition of 67 percent 1,3 butadiene, 27 percent solvent, 4 percent water and less than one weight percent of propyne, C-butene-2 and 1,2 butadiene. The overhead stream from tower 42 in line 43 would have a typical composition of 98 percent 1,3 butadiene, 0.7 weight percent propyne and less than 0.2 percent 1,2 butadiene. This composition is typical for lines 47 and 48, line 48 typically carrying five times the volume of line 47.

Referring to optional, but preferred lower withdrawal line 49, the composition in this line typically would be 30 percent solvent, 29 percent vinylacetylene, 16 percent 1,2 butadiene, 10 percent 1,3 butadiene, 8 percent butene-1 and 6 percent water. The reflux ratio between lines 57 and 56 is typically 5 to 1.

The bottoms from vessel 22 and third distillation zone 24 in line 58 are typically 90 percent solvent, 10 percent water. This composition is in reboiler line 59 and also lines 63 and 65. Typically, the amount of solvent in line 63 is typically two and one-half times the quantity in line 65.

Turning to the distillation flows between and internal of the vessels in FIG. 1, the vapor line 29 from the top of first distillation column or zone 21 to the bottom of the second distillation column 23 typically has a composition of 28 percent 1,3 butadiene, 24 percent isobutene, 13 percent butene-1, 11 percent C-butene-2, 10 percent T-butene-2, 6 percent solvent and 4 percent normal butane. The internal vapor stream going from the top of fourth zone 25 to the bottom of second zone 23 typically has a composition of 30 percent 1,3 butadiene, 20 percent isobutene, 17 percent C-butene-2, 13 percent T-butene-2, 9 percent butene-1 and 6 percent solvent.

The liquid line 31 from the bottom of second distillation zone 23 to the top of first distillation zone 21 typically has a composition of 65 percent solvent, 10 percent 1,3 butadiene, 7 percent water, 5 percent isobutene, 4 percent C-butene-2 and 3 percent T-butene-2, as well as 2 percent butene-1. The internal liquid downstream flow from the bottom of second distillation zone 23 to the top of fourth distillation zone 25 has essentially the same composition.

The vapor stream in line 32 from the upper portion of third distillation zone 24 to the bottom portion of first distillation zone 21 typically has a composition of 88 percent 1,3 butadiene, 6 percent solvent, 2 percent 1,2 butadiene, 2 percent propyne and slightly less than one weight percent of water. The internal vapor stream from the top of third distillation zone 24 to the bottom of fourth distillation zone 25 typically has the composition of the stream just given.

The liquid bottoms stream in line 30 from the bottom of first distillation zone 21 to the top of third distillation zone 24 typically has a composition of 61 percent solvent, 30 percent 1,3 butadiene, and 7 percent water and relatively small amounts of 1,2 butadiene, propyne and vinylacetylene. The internal liquid stream from bottom of fourth distillation zone 25 to the top of third distillation zone 24 typically has substantially the same composition.

When the vessels 20 and 22 of FIG. 1 are regarded as separate distillation columns, per se (assuming conventional internal liquid and vapor distribution means to achieve the flows previously recited therein), the process of this figure may be described as follows:

(1) A first feed stream 26 containing higher and lower boiling components is extractively distilled in a first distillation column 20 in the presence of an extractive solvent to separate a relatively high volatility overhead vapor stream 29 and a relatively low volatility bottoms liquid stream 30.

(2) Said overhead stream 29 and said bottoms stream 30 are supplied to an upper intermediate and a lower intermediate section, respectively, of the second distillation column 22.

(3) An extractive distillation is carried out in second column 22 also in the presence of said extractive solvent to separate more than two different volatility components.

(4) A liquid stream is recycled from said second column 22 in line 31 from adjacent the overhead stream 29 from the first column thereto back to the first column 20 at an upper level thereof.

(5) A vapor stream in line 32 is recycled from second column 22 from adjacent the bottoms stream in line 30 from the first column thereto back to the first column 20 at a lower level thereof.

(6) An overhead, highest voltility vapor stream is withdrawn through line 33 from the top of second column 22.

(7) An intermediate, next lower volatility stream, typically including some extractive solvent, is withdrawn through line 41 from said second column below the input of the overhead stream 29 from the first column and above the input 30 of the bottoms stream from first column 20.

(8) Optionally, but preferably, a lower, third lower volatility stream, particularly including some extractive solvent, is withdrawn via line 49 from the second column below the input of the bottoms stream 30 from first column 20.

(9) A lowest volatility liquid bottoms stream, including a preponderance of solvent, is withdrawn via bottoms line 58 from said second column 22.

(10) At least a portion of each of the second column top two withdrawal streams are passed out of the system and, if the third lower volatility stream and line 49 is taken off from tower or column 22, at least a portion thereof is also passed from the system (via lines 38, 47 and 56, respectively).

(11) The second column overhead vapor stream in line 33 is condensed and at least a portion thereof is recycled as reflux to an upper level of second column 22.

(12) At least a portion of the second column bottoms stream in line 58 is recycled to an upper level (line 63) of the second column substantially above the upper input thereto from the first column 20 in line 63 as a second feed stream to second column 22.

(13) Optionally, but preferably, a portion of the second column bottoms stream is passed via line 65 (and 27) to join the feed stream line 26 to first column 20.

(14) At least a portion of the extractive solvent from the second column intermediate withdrawal stream 41 is separated therefrom and recycled to an intermediate level of the second column in line 42a.

(15) If third lower volatility withdrawal stream line 49 is present, at least a portion of the extractive solvent therein is separated therefrom and recycled to a lower level of the second column via line 51.

(16) A portion of the second column liquid bottoms are preferably heated as at 60 to accomplish the distillations of the two columns. Specifically, a portion of the second column liquid bottoms are vaporized to provide the boilup for the distillation processes.

In the C4-butadiene recovery system, the side stream rectifier 50 shown is not preferred due to the problem of explosive excess of acetylenes in line 52. This is handled by blending with the raffinate of line 36 and water washing to extract solvent. This problem is not present in a C5 system.

FIG. 2

This figure illustrates the thermally coupled extractive distillation system of the previous figure as carried out in two towers where:

(1) The first tower or vessel has the first and second distillation zones therewithin, with the second distillation zone above the first distillation zone, and (2) The second column or tower has the third and fourth distillation zones therein with the fourth distillation zone positioned above the third distillation zone.

The generalized process description, as first given with respect to FIG. 1 is accurate with respect to this array and thus will not be redescribed. The compositions of the liquid and vapor flow streams between the various distillation zones as previously set forth with respect to a sample C4 feed stream is also accurate and will not be here restated. The first, second, third and fourth distillation zones and processes occuring therein and therebetween are essentially the same though relocated.

Figure 2:
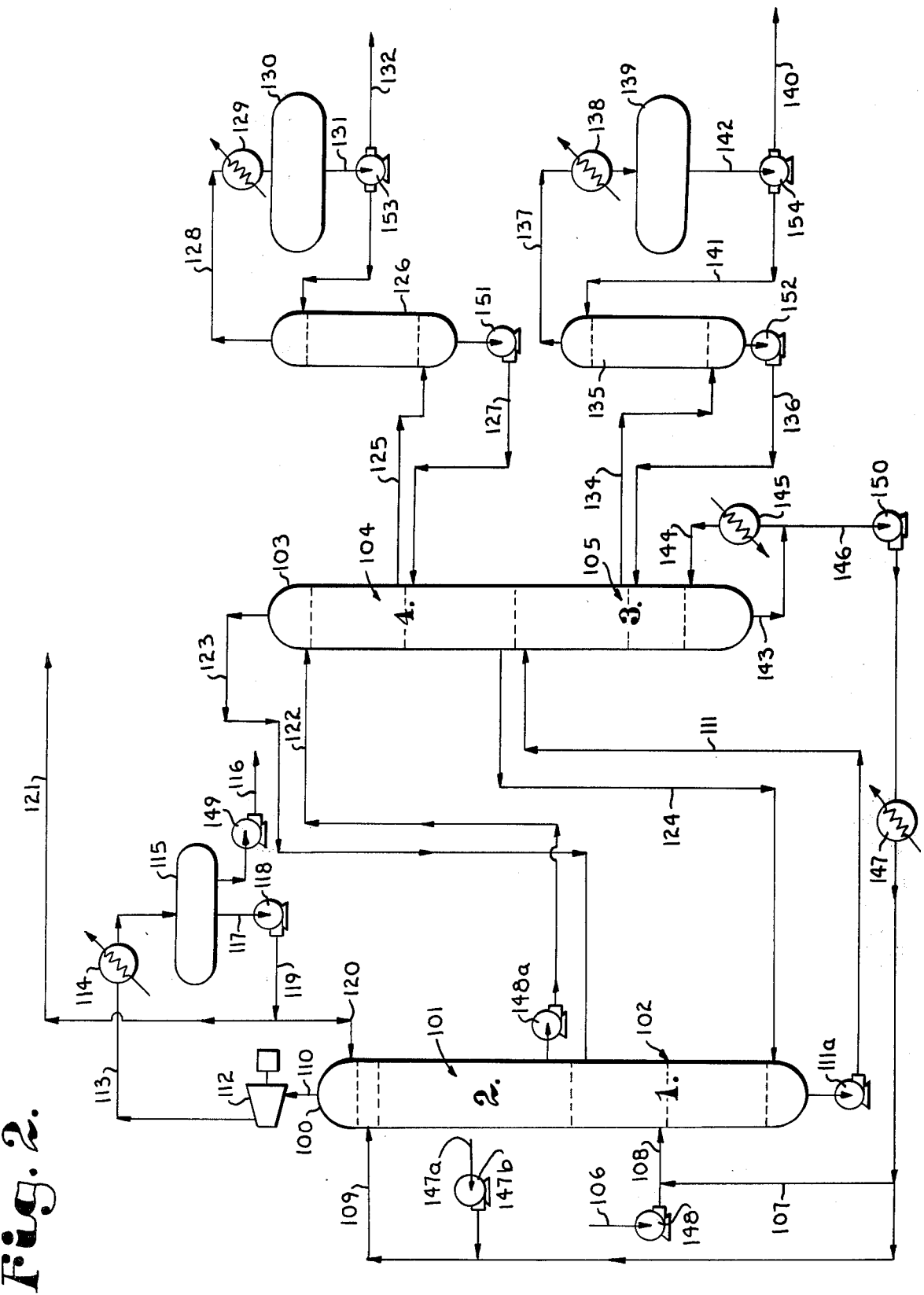
FIG. 2 is a second process embodiment of the subject distillation system utilizing two distillation towers wherein the first and second distillation zones are in a first vessel with the second zone positioned above the first and the third and fourth distillation zones are in a second tower with a fourth zone above the third.

Referring, then to FIG. 2, first vessel or tower 100 has upper, second distillation zone 101 and lower, first distillation zone 102 therein. Second vessel or tower 103 has upper, fourth distillation zone 104 therein and lower, third distillation zone 105 therein.

Returning to vessel 100, line 106 carrying a feed stream with higher and lower boiling components is optionally but preferably joined by solvent return line 107, the combined line 108 entering tower 100 intermediate the ends of first distillation zone 102 in the lower part thereof. Solvent recycle line 109 enters the vessel 100 at a top level of second distillation zone 101. Overhead vapor withdrawal line 110 passes from the top of second distillation zone 101. Liquid bottoms line 111 is taken off the bottom of vessel 100 from the lower end of first distillation zone 102.

Overhead line 110 passes to optional compressor 112, the discharge line 113, after condensation at 114, passing to receiver or accumulator vessel 115. Water draw-off line 116 is provided from vessel 115 and bottom withdrawal line 117 therefrom passes to pump 118, whose discharge line 119 splits into reflux return line 120 to the upper portion of vessel 100 and second distillation zone 101 and line 121 which passes out of the illustrated system.

Liquid withdrawal line 122 from the lower end of second distillation zone or column 101 passes to the upper portion of vessel 103 and fourth distillation column or zone 104 at the upper end thereof. Overhead vapor return line 123 from vessel 103 and the top end of fourth distillation zone 104 passes to the upper portion or end of the first distillation zone 102 in vessel 100.

Bottoms withdrawal line 111, after passing to pump 111a, goes to the upper end of third distillation zone 105 in vessel 103. Vapor line 124 passes from the upper end of third distillation zone 105 to the lower end of first distillation zone 102.

From fourth distillation zone 104 in tower 103, line 125 passes to the lower end of rectifier tower 126. Solvent return line 127, from the bottom of tower 126, returns to vessel 103 intermediate the ends of fourth distillation zone 104 closely adjacent line 125. Overhead line 128, after condensation at 129, passes to accumulator or receiver vessel 130. Bottoms line 131 from accumulator 130 feeds into line 132 out of system and reflux line 133 to the top of tower 126.

Optional but preferred withdrawal line 134 passes to the lower end of rectifier tower 135 from intermediate the ends of third distillation zone 105 on tower 103. The solvent recycle line 136 returns to third distillation zone 135 closely adjacent line 134 from tower 135. Overhead line 137 from tower 135, after condensation in condenser 138, passes to accumulator or receiver vessel 139. Liquid bottoms therefrom are split between system output line 140 and reflux line 141 to the top of tower 135, both fed by withdrawal line 142 from receiver 139. Water withdrawal lines (not seen) may be provided on both receivers 130 and 139.

Liquid bottoms line 143 from the lower end of third distillation zone 105 and tower 103 splits into reboiler return line 144 having heater 145 thereon and solvent return line 146. The latter line, with cooler 147 thereon, carries solvent, via line 109, into the top of tower 100 and has optional but preferred split off line 107 carrying solvent into main feed line 106. Make up solvent is provided as required in line 147a into line 109 using pump 147b.

Regarding towers 100 and 103 as themselves distillation columns, with the conventional liquid and vapor fittings thereon for the lines shown and described, the process in FIG. 1 may be described as follows:

(1) A first feed stream 109, predominantly comprising an extractive solvent and a second feed stream 106 containing higher and lower boiling components therein are extractively distilled in first distillation column 100 whereby to separate a relatively high volatility overhead vapor stream in line 110, an intermediate relatively lower volatility liquid stream 122 and a bottoms lowest volatility liquid stream 111.

(2) The first feed stream 109 is passed to an upper level of the first column at the top of second distillation zone 101 and the second feed stream 108 is passed to an intermediate level of the first column intermediate the ends of first distillation zone 102.

(3) The intermediate and bottoms streams 122 and 111, respectively, are supplied from said first column to an upper section and an intermediate section, respectively, of second distillation column 103, with the intermediate liquid stream passing from the bottom of second zone 101 to the top of fourth distillation zone 104 and the bottoms liquid stream 111 from the bottom of first zone 102 passing to the top of third distillation zone 105.

(4) An extractive distillation, also in the presence of the extractive solvent, is carried out in second column 103. The purpose of the distillations in the columns is to separate more than two different volatility components.

(5) Overhead vapor stream 123 from the top of second column 103 and the upper portion of fourth distillation zone 104 is recycled back to first column 100 at a level adjacent intermediate stream 122 therefrom and at the top of first distillation zone 102.

(6) An intermediate vapor stream 124 is recycled from the second column 103 at a level adjacent the bottoms stream 111 from the first column thereto back to the first column at a lower level thereof, that is, taken from the upper end of third distillation zone 105 to the lower end of first distillation zone 102.

(7) An overhead high volatility stream 110 is withdrawn from the top of the first column 100 and second distillation zone 101.

(8) An upper intermediate, next lower volatility stream 125, including some extractive solvent, is withdrawn from the second column between the inputs thereto from the first column, that is, intermediate the ends of fourth distillation zone 104.

(9) An optional, but preferred, lower intermediate third lower volatility stream 134, including some extractive solvent, is withdrawn from the second column below the inputs thereto from the first column (intermediate the ends of third distillation zone 105).

(10) A lowest volatility liquid bottoms stream, including a preponderance of extractive solvent, is withdrawn from the bottom of second column 103 in line 143 (from the bottom of third distillation zone 105).

(11) At least a portion of each of the first column overhead withdrawal stream 110, the upper intermediate second column withdrawal stream 125 and the lower intermediate withdrawal stream 134, if the latter is present, is passed from the system via lines 121, 132 and 140, respectively.

(12) The first column overhead vapor stream 110 is condensed at 114 and at a least a portion thereof is recycled to an upper level of the first column and second zone 101 in line 120 as reflux.

(13) At least a portion of the second column bottoms stream 146 is passed via line 109 to an upper level of the first column 100 and second zone 101 as a major portion of the first feed stream thereto.

(14) Preferably, but not necessarily, a portion of the second column bottoms stream is recycled via line 107 to join the second feed stream to the first column at 108.

(15) Optionally, the first column overhead vapor stream 110 may be compressed at 112 before condensing at 114.

(16) At least a portion of the extractive solvent in line 125 is separated from the contents of said line and recycled via line 127 to an intermediate level of the second column and fourth zone 104.

(17) If withdrawal line 134 is present, at least a portion of the extractive solvent in such line is separated therefrom in tower 135 and recycled via line 136 to a lower level of the second column and third zone 105 (or by other means as previously mentioned with respect to a C4-Butadiene system).

(18) Preferably, a portion of the second column liquid bottoms are heated at 145 to accomplish the distillation of the two columns.

While not specifically described, it is understood that there are internal up and down flows in towers 100 and 103 between zones 101 and 102 in the former and 104 and 105 in the latter. The upward flows are vapor and the downward flows are liquid.

Pumps 148, 148a–154 inclusive are employed on lines 106, 122, 116, 146, 127, 136, 131 and 142, respectively.

FIG. 3

Figure 3:
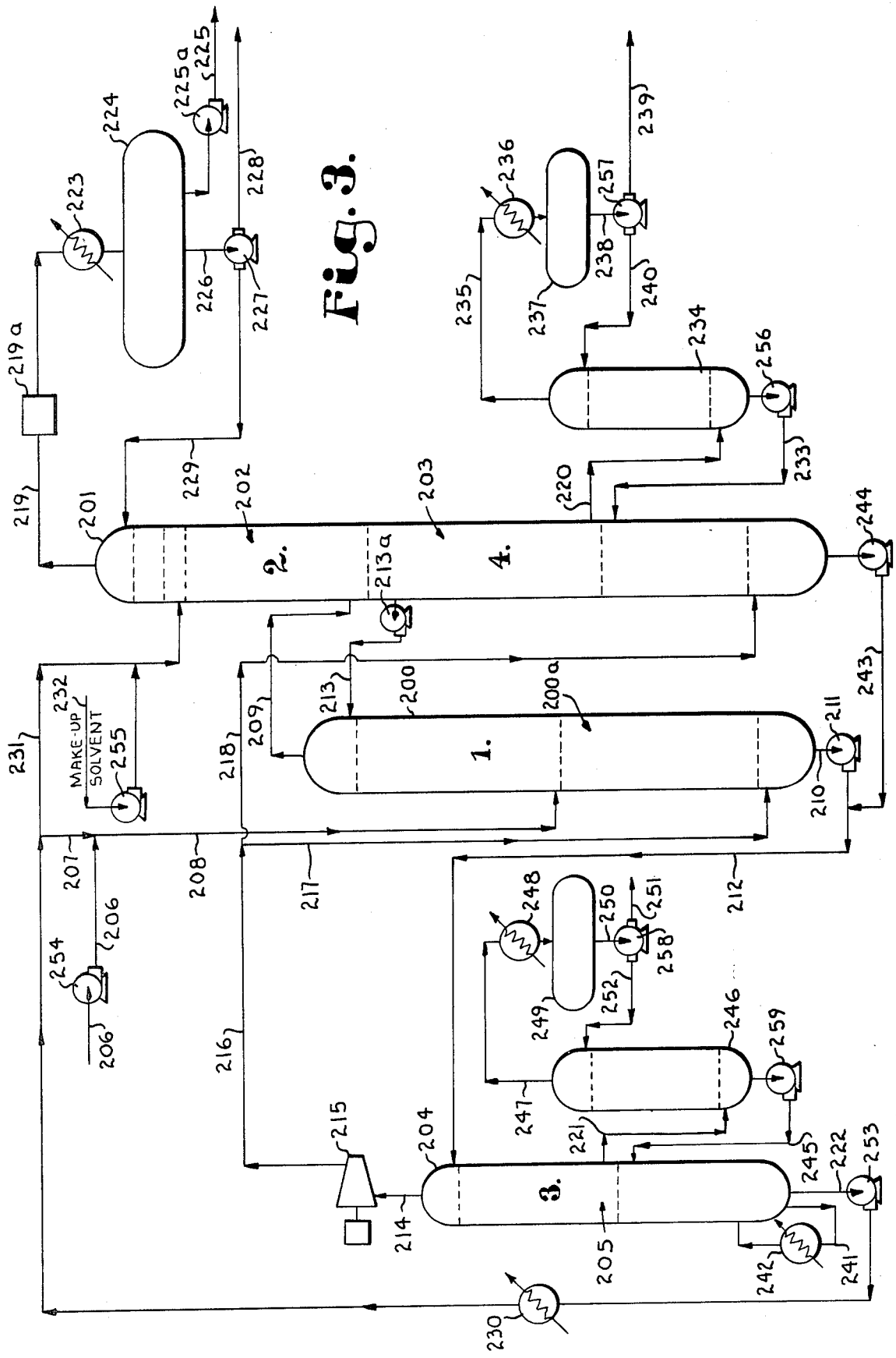
FIG. 3 is another form of the subject distillation process utilizing three distillation towers, the first and third distillation zones being in separate towers and the second and fourth distillation zones in a third tower with the second zone above the fourth zone therein.

FIG. 3 illustrates the thermally coupled extractive distillation system utilizing three towers to contain the four distillation zone. That is, a first tower or distillation column 200 contains first distillation zone 200a. A second tower or column 201 has second distillation zone 202 in the upper portion thereof and fourth distillation zone 203 in the lower portion thereof. A third distillation tower or column 204 has third distillation zone 205 therein.

The generalized process first described with respect to FIG. 1 also describes the process of FIG. 3, and will not be repeated here. The characteristics of the streams between and out of the distillation zones as set forth with respect to FIG. 1 also here applies and will not be redescribed (with respect to a sample C4 feed).

Regarding each tower, then of FIG. 3 as a distillation column, the process and flows thereof may be described as follow:

(1) A first feed stream 206 containing higher and lower boiling components may be joined by a solvent return line 207 (optionally) to provide a first feed line 208 into vessel 200 and first distillation zone 100 substantially intermediate the ends thereof. In first distillation column 200, then, this first feed stream, containing higher and lower boiling components, in the presence of an extractive solvent, is extractively distilled to separate a relatively higher volatility overhead vapor stream into line 209 and a relatively lower volatility bottoms liquid stream into line 210.

(2) Overhead stream and line 209 are passed or supplied to an upper intermediate section of second distillation column 201, that is, to the lower portion of second distillation zone 202.

(3) Bottoms line 210, using pump 211, is passed to the upper end of third distillation column 205 in the top of vessel 204 via line 212.

(4) Extractive distillations are additionally carried out in second and third distillation towers or columns 201 and 204, respectively, each also in the presence of the extractive solvent, to separate more than two different volatility components.

(5) A liquid stream in line 213 is recycled from second column 201 adjacent first column overhead stream thereto back to the first column at an upper level thereof, that is, from the bottom of second distillation zone 202 to the top of first distillation zone 200a. Pump 213a is positioned on said line.

(6) An overhead vapor stream in line 214 is passed overhead from third distillation column 204 and the top of third distillation zone 205 to optional compression at 215 and thence, via discharge line 216 from the compressor, through lines 217 and 218 to the lower ends of first and second distillation columns 200 and 201, respectively. That is, the vapor stream in line 216 is split into two parts and is passed via lines 217 and 218 from the upper end of third zone 205 to the lower ends of first and fourth distillation zones 200a and 203.

(7) An overhead, highest volatility vapor stream is withdrawn from the top of second column 201 and second distillation zone 202 via line 219.

(8) An intermediate, next lower volatility stream, including a substantial quantity of extractive solvent, is withdrawn via line 220 from second distillation column 201 below the input thereto of the overhead from the first column. Said otherwise, withdrawal line 220 passes a typically vapor stream from the fourth distillation zone 203 intermediate the ends thereof.

(9) An optional, but preferably intermediate, third lowest volatility stream, including an appreciable quantity of extractive solvent, is withdrawn via line 221 from the third distillation column 204 below the input of the bottoms stream 212 from the first column thereto. Said otherwise, withdrawal line 221 is taken off third distillation zone 205 intermediate the ends thereof via line 221.

(10) A lowest volatility liquid bottoms stream, including a preponderance of extractive solvent, via line 222, is withdrawn from the bottom of third column 204 and the bottom of fourth distillation zone 205.

(11) At least a portion of each of the overhead withdrawal stream 219, the intermediate fourth distillation zone withdrawal stream 220 and the intermediate third distillation zone 205 withdrawal stream 221 are passed out of the system, as will be described in detail with respect to each of them.

(12) The second column overhead vapor stream 219, after optional compression at 219a, is condensed at 223 and accumulated in vessel 224. Water may be withdrawn via line 225. Return line 226, using pump 227, splits into line 228 out of the system and reflux return line 229 to the top of second column 201 and second distillation zone 202. Pump 225a is positioned on line 225.

(13) At least a portion of the third column bottoms withdrawal stream in line 222, after cooling at 230, is passed via line 231 to an upper level of the second distillation column 201 and second distillation zone 202 substantially above the upper input 209 thereto from the first column as a second feed stream. Makeup solvent is added via line 232 as required.

(14) As previously described, a portion of the third column bottoms stream 222 may be recycled via line 207 to join first feed stream 206 to the first column in line 208.

(15) At least a portion of the solvent from the intermediate, next lower volatility withdrawal stream in line 220 from second column 201 and fourth distillation zone 203 may be separated and recycled via line 233 to an intermediate level of the second column close to the out take of line 220, that is, intermediate the ends of fourth distillation zone 203. This is accomplished by passing line 220 to a lower zone of rectifier tower 234. Overhead line 235, after condensation at 236 goes to receiver 237. Discharge line 238 therefrom splits into line 239 carrying product from the system and reflux recycle line 240 to the top portion of rectifier tower 234.

(16) At least a portion of the third column liquid bottoms are heated via reboiler line 241 having heater 242 thereon to accomplish the distillation of the three columns. This is the preferable, but not necessary arrangement. Reboilers may be supplied as desired, in all systems disclosed, as convenient and desired on the towers. For example, supplemental heat could be added via reboilers as the bottoms of zones 1 and 4. This is true for all systems here disclosed. Generally speaking this is not optimum heat use.

(17) At least a portion of the liquid bottoms from second column 201, via line 243 having pump 244 thereon, are passed from the second column and bottom of fourth distillation zone 203 to join the portion of the liquid bottoms via line 210 from first column 200 going to the third column in line 212. Thus liquid flows go from the bottoms of first and fourth zones 200a and 203 to the top of third zone 205.

(18) In the event that line 221 is employed (preferably) to withdraw a third lowest volatility withdrawal stream from third distillation zone 205 intermediate the ends thereof, at least a portion of the extractive solvent is separated from this stream and recycled via line 245 thereto closely adjacent line 221. Line 221 goes to the lower part of rectifier tower 246 and line 245 returns from the bottom thereof. Overhead line 247, after condensing at 248 goes to receiver 249. Line 250 from receiver 250 splits into withdrawal line 251 from the system and reflux recycle line 252. (In a C4 system, as previously noted, solvent return is achieved by a method other than rectifier tower 246.)

Not described, but present, are the rising vapor flow and falling liquid flow between distillation zones 202 and 203 (second and fourth) internal of vessel 201. In all rectifiers of all figures (thus 234 and 246 of this figure), there is the up and down counterflow of solvent poor and solvent rich fractions.

Pumps 253-259, inclusive are positioned on lines 222, 206, 232, 233, 238, 250, and 245 respectively.

FIG. 4

Figure 4:
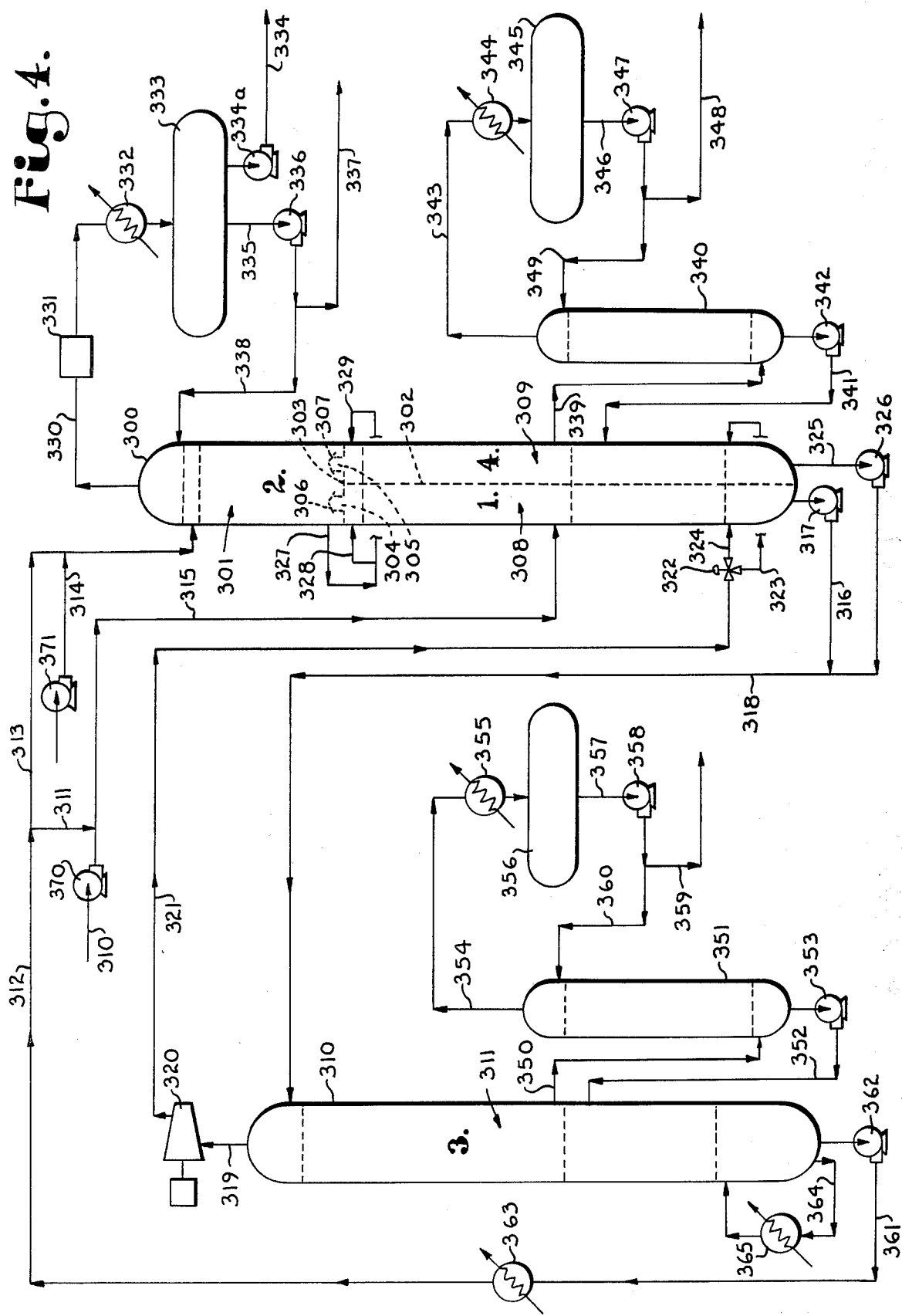
FIG. 4 shows a fourth version of the subject distillation process wherein the distillation zones are in two towers, the third zone in a separate tower, while the first, second and fourth distillation zones are in a second tower, the first and fourth distillation zones being in the lower portion of the second vessel divided from one another, the second zone positioned thereabove.

FIG. 4 discloses the thermally coupled extractive distillation process carried out in a pair of towers, one of them partitioned to enable it to contain therein the first, second and fourth distillation zones of the character previously described. The third distillation zone is contained in the second tower. The generalized description of the process made with respect to FIG. 1 here also applies. It will not be repeated. The characterization of the internal and external tower streams with respect to content of a typical C4 feed stock is also here applicable and will not be redescribed. While some of the flow streams among the figures vary internally and externally depending on tower structure, between the zones they are invariant.

Turning, then, to FIG. 4, first tower 300 has second distillation zone 301 in the upper portion thereof. The lower end of tower 300 is subdivided vertically by impermeable wall 302, which runs over half the length of tower 300 from the bottom end thereof. Intermediate wall 303 has chimneys 304 and 305 with deflectors 306 and 307 positioned thereover, permitting flow thereunder.

In the view shown, first distillation zone 308 is defined on the left side of internal wall 302 and fourth distillation zone 309 on the right hand side thereof. Both first and fourth distillation zones 308 and 309 may discharge vapor overhead through chimneys 304 and 305, respectively, into the lower end of zone (second distillation zone) 301.

Second vessel 310 has third distillation zone 311 therein.

The basic higher and lower boiling component feed stream, typically a C4 feed, comes into the system through line 310 and is optionally, but preferably, joined by solvent recycle line 311 from main solvent recycle line 312. The main solvent feed line to the top portion of second distillation zone 301 is line 313 with makeup solvent input line 314 thereon. The C4 feed (with optional solvent) line to the middle of first distillation zone 308 is line 315. With these basic vessels, distillation zones and feed inputs noted, the process as carried out in the system of FIG. 4 may be described as follows:

(1) Feed stream 315 containing higher and lower boiling components (and optionally extractive solvent) is extractively distilled in first distillation zone 308 to separate a relatively high volatility overhead vapor stream passing out chimney 304 and a relatively low volatility bottoms liquid stream taken off through line 316. This distillation is in the presence of extractive solvent, then 328 via line 313.

(2) The overhead stream up chimney 304 is passed thereat into the lower portion of second distillation zone 301 which comprises the upper undivided part of first vessel 300.

(3) The bottoms stream in line 316, using pump 317, is passed via line 318 to an upper section or level of third distillation column 311 in second vessel 310.

(4) An overhead vapor stream through line 319 from the top portion of third distillation zone 311 and vessel 310 passes to optional compressor 320. The discharge line 321 from compressor 320 is split at valve 322 into lines 323 and 324 which pass, respectively, to the lower ends or portions of fourth distillation zone 309 and first distillation zone 308, respectively.

(5) As previously stated, a second feed stream of predominantly extractive solvent in line 313, with makeup solvent as is required from line 314, is passed to the upper part of second distillation zone 301.

(6) The upper ends of the first and fourth distillation zones or columns 308 and 309, respectively, are in flow communication with the lower end of second distillation zone 301 through chimneys 304 and 305.

(7) A liquid bottoms stream in line 325 is passed from fourth distillation zone 309, using pump 326 to join common line 318 passing to the upper section of third distillation zone 311.

(8) A liquid stream in line 327 is passed from a lower portion of the second distillation zone 301 via lines 328 and 329 to the upper portion of each of the first and fourth distillation zones 308 and 309, respectively.

(9) Extractive distillations are also carried out in the second, third and forth distillation zones 301, 311 and 309 also in the presence of said extractive solvent.

(10) An overhead, highest volatility vapor stream is taken off via line 330 from the top of second distillation zone 301. After an optional compression step at 331 and condensation at condenser 332, this stream is passed to a receiver or accumulator vessel 333. Line 334 removes water from vessel 333. Bottom withdrawal line 335, using pump 336, splits thereafter into line 337 passing from the illustrated system and return reflux line 338.

(11) An intermediate, next lower volatility stream, including an appreciable quantity of extractive solvent, is withdrawn from the fourth distillation column 309 intermediate the ends thereof via line 339. This line passes to the lower portion of rectifier tower 340. Bottoms line 341, using by pump 342, returns the solvent rich stream intermediate the ends of fourth distillation zone 309 close to line 339. Overhead line 343, after condensing at 344, is passed to receiver vessel 345. Bottoms line 346, using pump 347 thereafter splits into line 348 out of system and overhead reflux recycle line 349.

(12) An intermediate, third lower volatility stream, including an appreciable quantity of extractive solvent, is withdrawn via line 350 from vessel 310 and third distillation column 311 intermediate the ends thereof, passing to rectifier tower 351. Solvent rich bottoms are recycled via line 352 from tower 351 using pump 353. This recycle passes back to third distillation zone 311 closely adjacent output line 350. Overhead line 354, solvent poor, is condensed at 355 and accumulated in vessel 356. Bottoms line 357, using pump 358, splits into line 359 going out of system and reflux return line 360 to the top portion of rectifier tower 351.

(13) A lowest volatility liquid bottoms stream, predominantly comprising extractive solvent, is withdrawn via line 361 from the bottom of distillation tower 310, the lowest portion of third distillation zone 311. This line, using pump 362, after cooling at 363 becomes main solvent line 312 to the system.

(14) As previously stated, at least a portion of the overhead withdrawal stream 330 from the second column or zone 301, the intermediate withdrawal stream 339 from fourth distillation zone 309 and intermediate stream 350 from third distillation zone 311 are passed out of the system via lines 337, 348 and 359, respectively.

(15) The second distillation zone overhead vapor stream through line 330 is condensed at 332 and at least a portion thereof recycled via line 338 to an upper level of the second distillation zone 301 as reflux.

(16) As also previously mentioned, at least a portion of the third column bottoms withdrawal stream 351 is recycled via line 313 to an upper level of the second distillation zone 301 as a major portion of the feed stream thereto.

(17) A portion of the third column bottoms recycle stream is optionally passed via line 311 to join feed stream 310 in line 315 to the first distillation zone 308.

(18) At least a portion of the extractive solvent from the fourth distillation column withdrawal stream 339 and the third distillation column withdrawal stream 350 is preferably separated from the streams and recycled to intermediate levels of the fourth and third distillation columns respectively, through lines 341 and 352, as previously described.

(19) A portion of the liquid bottoms of third distillation zone 311 and vessel 310 are passed in line 364 through reboiler 365 where they are heated and vaporized, at least in part, to accomplish the distillation in the four distillation zones of the two vessels.

Pumps 370 and 371 are provided on lines 310 and 314, respectively.

FIG. 5

Figure 5:
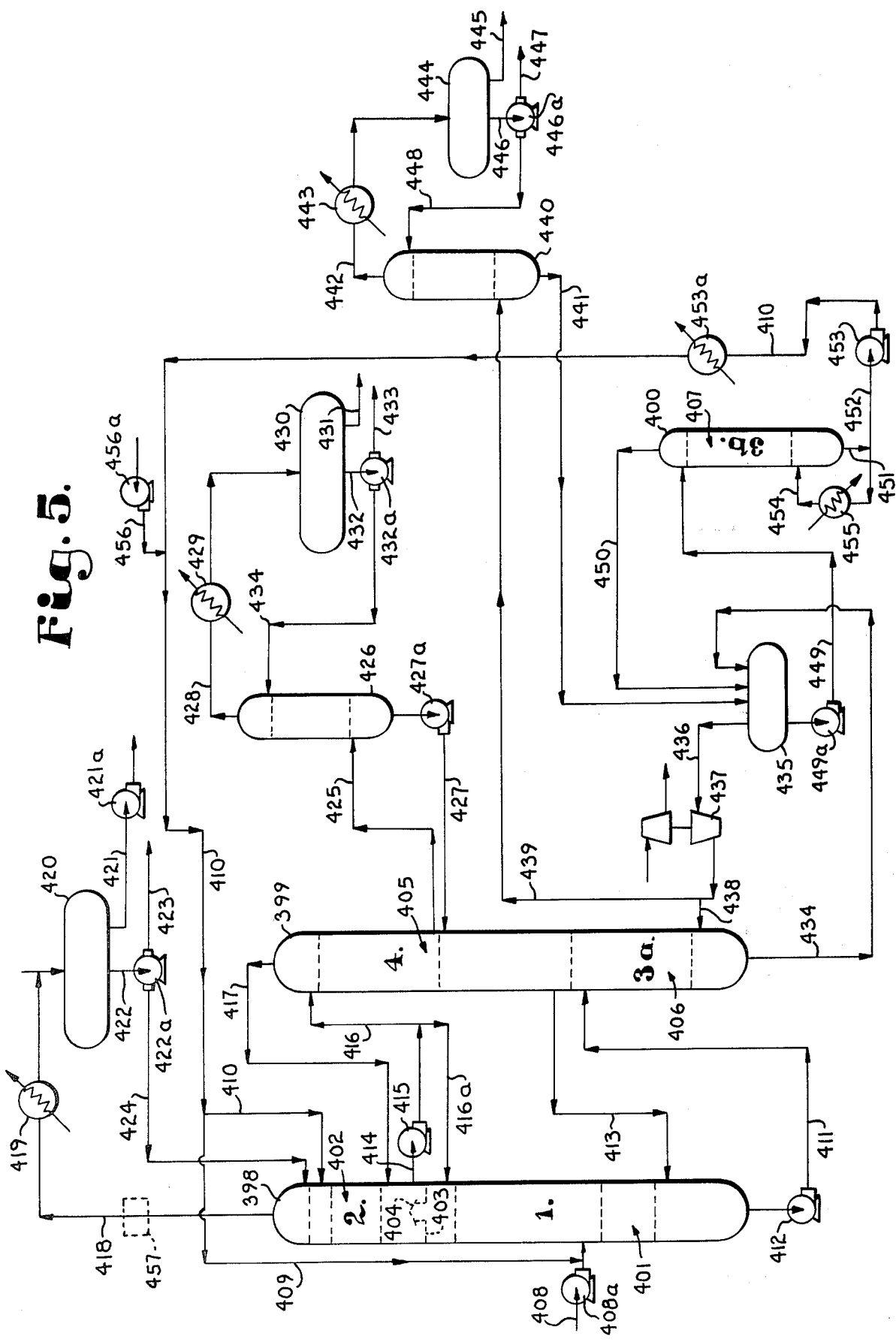
FIG. 5 shows a thermally coupled extractive distillation system analogous to that seen in FIG. 2, but wherein the third distillation zone is divided into two parts, the upper portion thereof in the second tower below the fourth distillation zone, the lower part of the third distillation zone in a third tower.

FIG. 5 shows a system where the third distillation zone is split between two vessels. This system is particularly adapted to a C5 feed stream, although it may also be employed with C4 feed streams, as is the case with all the systems of FIGS. 1-4, inclusive.

FIG. 5 again will be particularly described with respect to the four distillation zones, one of which (zone 3) is here split into upper and lower parts in separate vessels with a vapor withdrawing flash drum and associated compressor coupled therewith. The characterization of a typical C4 feed process with respect to the particular zone flows and compositions is again the same and will not be repeated. Distinctions are hereafter set forth.

Referring to FIG. 5, therein are shown three distillation vessels or towers 398, 399 and 400. In tower 398, first distillation zone 401 is provided in the lower portion thereof and second distillation 402 in the upper portion thereof. Horizontal internal wall 403 with chimney 404 therein defines the lower and upper limits of the two zones.

In tower 399, the fourth distillation zone 405 is provided in the upper portion of the vessel and the upper portion 406 of the third distillation zone. This will be referred to as zone 3A. Tower 400 has the lower portion of the third distillation zone (or 3B) therein as at 407.

It may thus be seen that the flow diagram of FIG. 5 is substantially like that of FIG. 2, with the exception that third distillation zone 406, 407 is in two towers or vessels, rather than a single vessel. The linkage of these partial zones with one another is also different.

Main feed line 408 carries (typically, C4 or C5 feed) higher and lower boiling components containing stream to be separated therein, this line, after optional joinder by solvent recycle line 409, passing to tower 398 intermediate the ends of first distillation zone 401. Extractive solvent input line 410 passes to a top portion of tower 398 and an upper level of second distillation zone 402.

Liquid bottoms line 411, having pump 412 thereon, passes from the bottom of tower 400 and first distillation zone 401 to an upper portion of third distillation zone 406 in tower 401. Vapor line 413 passes from the upper end of third distillation zone 406 and tower 401 to a lower portion of first distillation zone 401. Internally of tower 401, there is a liquid downstream from fourth distillation zone 405 to third distillation zone 406, as well as a vapor stream from the top of third zone 406 to the bottom of fourth zone 405.

Liquid withdrawal line 414 from the bottom of second distillation zone 402 in vessel 398 has pump 415 thereon. After the pump, this line splits into line 416 passing liquid to the top portion of fourth distillation zone 405 and vessel 399 and line 416a passing liquid to the top portion of first distillation zone 401. Vapor withdrawal line 417 passes vapor overhead from fourth distillation zone 405 to a lower portion of second distillation zone 402 in tower 398.

Vapor withdrawal line 418 from the top of tower 398 and second distillation zone 402 passes to condensation at 419 and then to accumulator or receiver 420. Water withdrawal line 421 and material withdrawal line 422 lead from accumulator 420. Line 422 splits into out of system line 423 and recycle reflux line 424 to the upper portion of tower 398 and second distillation zone 402.

From tower 399, next volatile material withdrawal line 425 (less volatile than vapor line 418) passes to rectifier tower 426. Solvent rich recycle bottoms are carried back to tower 399 via recycle line 427. Line 425 is taken off from and line 427 returns to fourth distillation zone 405 substantially intermediate the ends thereof. Overhead line 428, carrying solvent poor material, is condensed at 429, thereafter passing to accumulator 430. Vessel 430 may have water withdrawal line 431. Material withdrawal line 432 from the bottom of vessel 430 splits into out of system line 433 and reflux recycle line 434.

Liquid bottom withdrawal line 434 from the bottom of tower 399 and the bottom of the upper third distillation zone 406 passes to accumulator 435. Vapor line 436 passes to compressor 437 and thereafter splits into solvent lean vapor line 438 intermediate the ends of upper third distillation zone 406 and line 439 which passes to rectifier tower 440. Solvent rich bottoms stream 441 from tower 440 returns to accumulator 435. Solvent poor overhead line 442, after condensation at 433, passes to receiver 444. Receiver 444 may have water withdrawal line 445. Material withdrawal line 446 of vessel 444 splits into line 447 out of system and reflux recycle line 448 back to the upper portion of rectifier tower 440.

Liquid bottoms from accumulator 435 are taken out by line 449, using pump 449a, and passed to the upper portion of tower 400 which contains the lower part 407 of the third distillation zone. Relatively solvent poor overhead vapor line 450 returns to receiver 435. Liquid bottoms withdrawal line, solvent rich, at 451 splits into solvent recycle line 452, using pump 453 and reboiler line 454. The latter has steam heater 455 thereon, returning to a lower portion of tower 400. Solvent recycle line 452, after pump 453, splits into line 410 passing the main solvent feed to the upper portion of vessel 398 and the upper level of second distillation zone 402 and optional (but preferred) solvent recycle line 409 joining main feed line 408. Solvent make-up is added through line 456 using pump 456a to line 410. Cooler 453a is provided on line 410.

In a C4 system, it should be noted that the composition of the vapor in line 436 is substantially that of line 49 in FIG. 1. The composition of reclaimed solvent in line 452 is the same as that in line 58 of FIG. 1.

Pumps 408a, 421a, 422a, 427a, 432a, 446a, 449a and 456a are provided on lines 408, 421, 422, 427, 432, 446, 449 and 456 respectively.

The process of FIG. 5 may be described with respect to the distillation zones as follows:

(1) A feed stream 408 containing higher and lower boiling components is extractively distilled in a first distillation zone 401 in the presence of extractive solvent (from line 409 and/or vessel 399) to separate a relatively low volatility liquid bottoms stream in line 411 therefrom and a relatively higher volatility overhead vapor stream.

(2) The overhead stream noted passes through chimney 404 to the lower portion of second distillation zone 402 and the bottoms stream via line 411 to the upper portion of third distillation zone 3A and 406.

(3) A first vapor stream from the upper third distillation zone 406 would pass in vessel 399 to the lower level of fourth distillation zone 405. A second overhead vapor stream from upper third zone 406 passes via line 413 to a lower level of first distillation zone 401. (4) A second feed stream of predominantly extractive solvent is passed via line 410 to an upper zone of second distillation zone 402.

(5) A first liquid stream from the lower portion of second distillation zone 402 is passed via lines 414 and 416a to the upper level of first distillation zone 401. A second liquid stream is passed from said lower portion of second zone 402 to the upper level of fourth distillation zone 405 via line 416.

(6) A liquid stream is passed from the lower portion of fourth zone 405 in vessel or tower 399 to the upper portion of third zone 406.

(7) Extractive distillations in the second zone 402, upper third zone 406, lower third zone 407 and fourth zone 405 are also carried out in the presence of the extractive solvent.

(8) A highest volatility overhead vapor stream is withdrawn from the top of second zone 402 through line 418.

(9) An intermediate, next lower volatility stream, including a significant proportion of extractive solvent, is withdrawn from fourth zone 405 intermediate the ends thereof through line 425.

(10) An intermediate, third lower volatility stream, including some extractive solvent, is withdrawn from the third distillation column zones 406 and 407 via line 439 (out of vessel 435 receiving line 434 and 450.).

(11) A lowest volatility liquid bottoms stream, predominantly comprising extractive solvent, is withdrawn from the lower distillation zone 3B and 407 through lines 451 and 452.

(12) At least a portion of overhead withdrawal stream 418 is passed out of the system via line 423. At least a portion of the intermediate withdrawal stream from the fourth zone of line 425 is removed from the system via line 433. At least a portion of the intermediate withdrawal stream from line 439 is taken out of the system via line 447.

(13) The second distillation zone 402 overhead vapor stream in line 418 is condensed and at least a portion thereof is recycled as reflux in line 424 to an upper level of the second distillation zone 402.

(14) At least a portion of the third zone 407 bottoms withdrawal stream is recycled to an upper level of second distillation zone 402 through line 410.

(15) A portion of the lower third zone 407 bottoms stream 452 is optionally, but preferably, recycled via line 409 to join the feed stream 408 to the first distillation zone 401.

(16) A portion of the solvent in the stream in line 425 from fourth zone 405 is recycled in line 427 to an intermediate level of fourth zone 405.

(17) A portion of the solvent in the intermediate third lower volatility stream in line 439 is separated in column 440 and recycled via line 441 to vessel 435 and thus via line 449 to lower third distillation zone 407.

(18) A portion of the lower third zone 407 liquid bottoms in 451 are heated in reboiler 455 and returned via line 454 to accomplish distillation in the four columns.

(19) Optionally, the overhead vapor stream in line 418 from the top of second zone 402 may be compressed at 457 before condensing at 419.

FIG. 6

Figure 6:
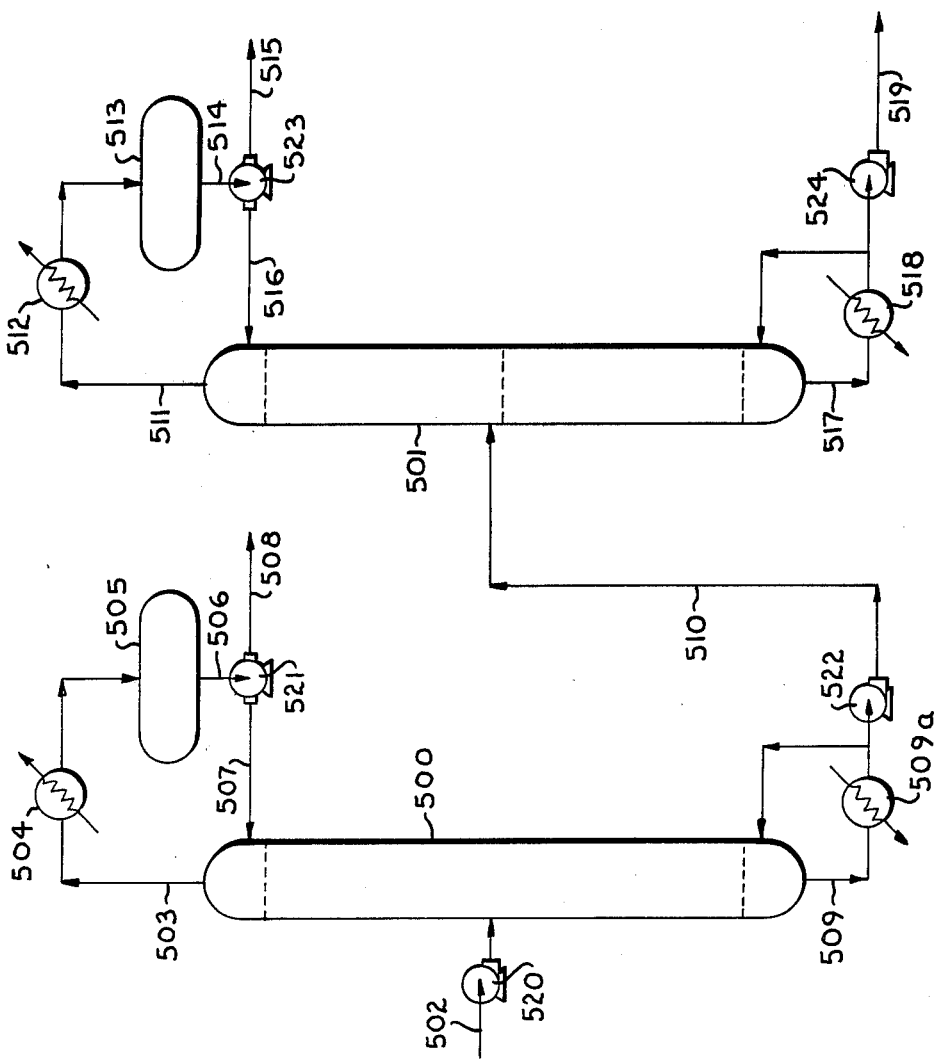
FIG. 6 shows a conventional distillation system adapted to take the system product, such as butadiene, and separate low boiling and high boiling impurities therefrom to obtain the desired ultimate product.

Referring to FIG. 6, therein is shown a simple distillation step for producing an ultimate product from the butadiene side stream of the various figures. This is the stream from line 47 in FIG. 1, line 132 in FIG. 2, line 239 in FIG. 3, line 348 in FIG. 4 and line 447 in FIG. 5. A typical stream in this line will comprise 98.36 weight percent 1,3 butadiene, 0.73 percent propyne, 0.427 percent C-butene-2, 0.221 percent of propadiene and parts per million of T-butene-2, water, butyne-1 and solvent (ACN) in decreasing amounts.

Towers 500 and 501 are provided. Feed stream 502 of character described passes to vessel 500. Overhead stream in line 503 contains low boiling impurities such as propyne and propadiene. This stream is condensed at 504 and collected in receiver 505. Withdrawal stream 506 splits into reflux return line 507 and low boiling impurity out of system line 508. Bottoms 509 are reboiled at 509a and line 510 passes to the center of vessel or tower 501.

In tower 501, the overhead light stream is taken off through line 511, condensed at 512 and collected in receiver 513. Withdrawal line 514 splits into out of system line 515 carrying purified product 1,3 butadiene at least 99.5 percent by weight. Reflux return line 516 is the other side of the split back to the top of tower 501. Bottoms line 517 is reboiled at 518 with withdrawal line 519 carrying off high boiling impurities including cis butene 2,1,2 butadiene and butyne-1.

In ultimate product stream 506, there may be 0.45 weight percent C-butene-2 and parts per million of T-butene-2,1,2 butadiene, butyne 1, propadiene and propyne in decreasing order (627, 38, 11, 8 and 8 ppm, respectively).

Pumps 520-524 inclusive are provided on lines 502, 506, 510, 514 and 519, respectively.

TOWER PRESSURE

The various figures show optional compressors at various points with respect to the main distillation towers. Thus, FIG. 1 shows optional compressor 40 on line 33. FIG. 2 shows optional compressor 112 on line 110. FIG. 3 shows optional compressor 219a on line 219 and optional compressor 215 on line 214.

At this point, it is noted that only one of the two optional compressors shown in any system will be used at a given time, that is, either off the top zone 2 or off the top of zone 3. Normally, they will not be used together.

FIG. 4 again shows optional compressor 331 on line 330 and optional compressor 320 on line 319. The previous remarks also hereapply. FIG. 5 shows necessary compressor (for this system) 437.

For C4 systems without either compressor, or on the discharge side of a compressor, the towers are run at 50 to 60 psig. For C4 systems upstream of a compressor, the towers are at 15 to 20 psig.

In the event that a compressor is put at the top of the tower of zone 2, it is not feasible to use cooling water or plant water for the condensers off the rectifier towers for the butadiene and acetylene (equivalent) lines. Chilled water or refrigeration could be used. Another option with respect to the rectifier towers shown in the various systems illustrated, not discussed in detail here, but well understood by those skilled in the art, would be to withdraw a liquid stream rather than a vapor stream from the zone in question and use a pump to feed such a stream to the rectifier tower. In such a case there is the option of partially vaporizing the liquid stream to the rectifier or using a reboiler on the bottom of the rectifier towers. In the case of FIGS. 3 and 4, in a C4 butadiene system if compressor 215 or 320 is employed off the top of the tower containing zone 3, then a rectifier as seen at 246 and 351 in the two figures would normally not be employed and another solvent separation system such as washing would be employed, instead of the solvent separation step shown on the acetylene draw-off line.

FIG. 7

Figure 7:
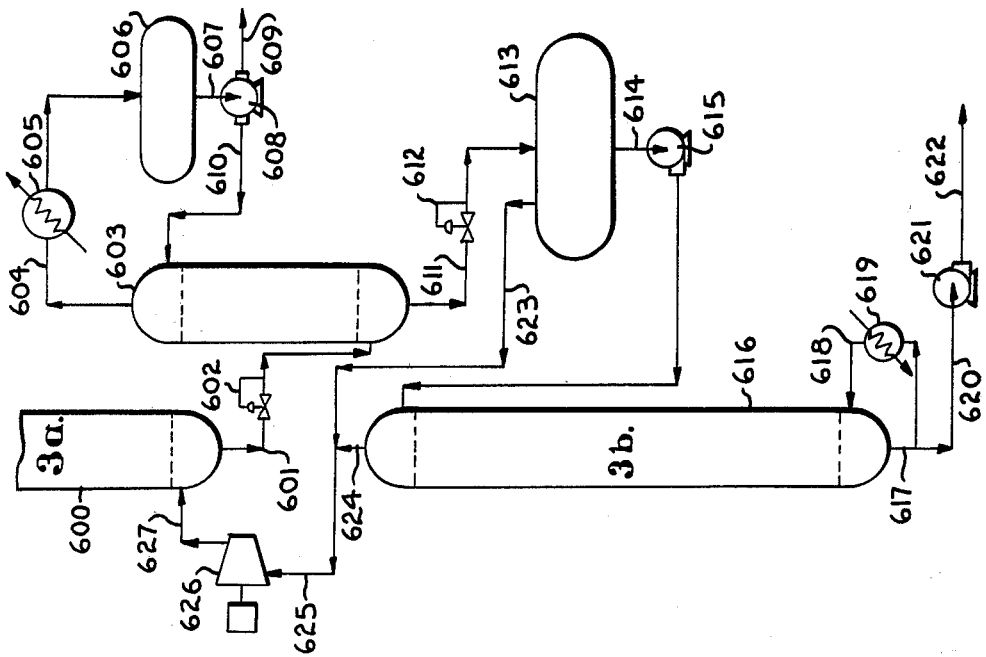
FIG. 7 is a fragmentary schematic flow diagram showing a variation of the system of FIG. 5. Specifically.

FIG. 7 illustrates a variation of the system of FIG. 5, particularly with respect to the subdivision of zone 3 into a separate tower for the lower portion thereof, or distillation zone 3b. The drawing of FIG. 7 is assumed to be the same as FIG. 5 with the tie in link being that the fragmentary lower portion of the tower in the upper left hand corner of FIG. 7 is the bottom of tower 399 of FIG. 5 or 3a. All the equipment of FIG. 5 that is tied to the bottom of tower 399 in the view is replaced by that of FIG. 7 in this variation.

Referring, then to FIG. 7, tower 600 has bottoms withdrawal line 601 with back pressure valve 602 thereon. Line 601, after valve 602, passes to the lower portion of distillation tower 603. Overhead vapor line 604 is condensed at 605, thereafter passing to receiver 606. Line 607 then passes to pump 608. From pump 608, line 609 goes out of system carrying the acetylene cut equivalent to line 439 of FIG. 5. Reflux return line 610 passes to the top of tower 603.

Bottoms line 611 has back pressure valve 612 thereon, thereafter passing to receiver 613. Bottoms withdrawal line 614 has pump 615 thereon and thereafter passes to the top of tower 616. Tower 616 is the lower portion of zone 3 and thus is designated 3b.

Bottoms line 617 splits into recycle line 618 having reboiler 619 thereon and solvent return line 620 having pump 621 thereon. This line, 622 after pump 621, is equivalent to line 410 in FIG. 5 and goes back to an upper part of zone 2, optional solvent recycle line 409 to join hydrocarbon feed line 408 to zone 1 also being taken thereon.

Overhead line 623 from flash drum 613 and overhead line 624 from distillation vessel 616 (zone 3b) join in line 625 passing to compressor 626. Compressor discharge line 627 is passed to the bottom of vessel 600 and zone 3a.

In FIG. 7, the solvent downstream from the equivalent of vessel 399 in FIG. 5 is passed via bottoms line 601 to tower 603. Valve 602 permits flashing of hydrocarbons therefrom. The hydrocarbon overhead from vessel 603 is the acetylenes cut which goes out of system via line 609.

Bottoms line 611 from tower 603, carrying solvent, passes through back pressure valve 612, thus flashing hydrocarbons in drum 613. Solvent bottoms from drum 613 pass to the top of tower 616, zone 3b. Solvent recycle is taken off bottom line 617. The overhead vapor flows from drum 613 and tower 616, in lines 623 and 624, are compressed and returned to the bottom of tower 600, going to the bottom of zone 3a in tower 399 in FIG. 5.

The reboiler 619 on tower 3b (616) provides the vapor for the distillation in all the towers of the system of FIG. 7 and associated towers like those in FIG. 5 associated therewith. Because of the lowered temperature in 3b (tower 616) made possible by the FIG. 7 improvement, the solvent may be protected from excessive degradation due to heating in reboiler 719 (reduction of pressure into zone 3b through valves 602 and 612 and vessels 603 and 613). Further, fouling of the trays and reboilers due to polymerization may be minimized in this system.

GENERAL CONSIDERATIONS

In FIGS. 2 and 5, the basic distillation towers (100 and 103 in FIG. 2 and 398 and 399 in FIG. 5) can be run at different pressures by dropping the pressure on the vapor streams from towers 103 and 399 that is, one can independently control the vapor flow from zone 3 to zone 1 and zone 4 to zone 2, which give optimum stability and control in the system.

Thus it is seen that, with respect to a C4 rich hydrocarbon fraction, containing paraffins, olefins, diolefins and acetylenes, the disclosed system will separate a top paraffin-olefin rich fraction (raffinate), a diolefin stream rich in 1,3 butadiene, a mixed diolefin-acetylene stream rich in 1,2 butadiene and acetylene and a solvent rich fraction. In the event that two intermediate streams are not taken off zones 4 and 3 separately, the single cut would combine the diolefin stream rich in 1,3 butadiene and the mixed diolefin-acetylene rich in 1,2 butadiene and acetylenes. If the latter is the case, such combined stream would be separated by conventional distillation after drawoff.

In a C5 system, which particularly includes cyclodiolefins, the above noted diolefin stream rich in 1,3 butadiene would be, instead, a diolefin stream rich in isoprene. The mixed diolefin-acetylene stream would be rich in piperylenes, cyclopentadiene and acetylenes.

With respect to the use of a compressor, alternatively, either at the top of zone 2 or zone 3, in all cases, the use of the compressor is to lower the pressure and temperature in the towers upstream of the compressor. When the compressor is used at the top of zone 2 (for example, at 40 in FIG. 1, 112 in FIG. 2, 219a in FIG. 3, 331 in FIG. 4, 457 in FIG. 5), the entire tower system before the compressor is under reduced pressure. In a hydrocarbon system such as a C4 or C5 cut, there is little problem with respect to this compressor fouling as the relatively clean, light hydrocarbons are not such as to creat a polymerization problem. The systems of FIGS. 1 and 2, then, are optimum for the use of the compressor at the top of zone 2.

FIGS. 3 and 4 show systems where use of (FIG. 3) a compressor at 215 or (FIG. 4) a compressor at 320 make possible condensation of the top withdrawals (223 and 236 in FIG. 3 and 332 and 334 in FIG. 4) with cooling water. Further, the use of such compressor enables the use of lesser size towers following the compressor as at 200, 201 and 234 in FIG. 3. The price, as it were, of this set of advantages with respect to FIGS. 3 and 4 is that the compressors 215 or 320 may be in a fouling service and periodic cleaning or a spare compressor may be required. That is, polymerization may be a problem, creating compressor fouling, at these locations.

With respect to FIG. 5, compressor 437 is in possible fouling service (requiring a spare compressor or periodic cleaning, possibly), but with its use, all four towers 398, 399, 426 and 440 may be smaller. Additionally, condensers 419, 429 and 443 may use cooling water.

Again, with respect to FIG. 7, which is a modification of the FIG. 5 system, compressor 626 is in fouling service along the lines set forth above. The selection of pressure on tower 603 via valve 602 may be to be able to use cooling water at 605. It this figure, because of the presence of compressor 626, towers 398, 399 and 426 are smaller. Tower 603 substitutes for tower 440 and is larger than tower 440 because of its intermediate pressure operation. In a C4 system, the compositions of lines 609 and 622 in FIG. 7 are the same as lines 447 and 452 of FIG. 5.

ZONE CHARACTERIZATION

Other than as previously set forth, the following remarks may be made with respect to the four distillation zones generally, with respect to each of the systems involved.

The immediately following remarks apply to butadiene recovery from a C4 system.

Distillation zone 1 has sufficient boil-up and reflux (with solvent) and the required number of trays to adequately separate the heaviest acetylenes relative to the net 1,3 butadiene flow from the top of this trayed section. Likewise, the separating power of this zone is such that the required amount of paraffins and olefins are removed with respect to the net flow of 1,3 butadiene out the bottom of this trayed section. The basic separation requirement is to limit the amount of heavy acetylenes which are carried overhead from zone 1 and the amount of light olefin-paraffin hydrocarbons which pass downwardly out of this system to a certain minimum. I have found that, if one third of the quantity of each of the noted compounds (heavy acetylenes overhead out of zone 1 and light paraffin-olefin bottoms out of zone 1) permitted in the ultimate product is permitted to pass in each noted stream, then, such basic cut in zone 1 will enable efficient working of the entire system.

Zone 2 has sufficient trays and reflex (with solvent) to adequately removed the paraffins-olefin stream as an overhead product while holding 1,3 butadiene distillation losses within specification.

Zone 4 is that from which the butadiene concentrate is withdrawn from the system as a side stream vapor. Zone 4 has sufficient trays and reflux (with solvent) to produce a high quality butadiene concentrate. The trayed section above the product draw point serves to reject paraffins and olefins from the net 1,3 butadiene fed to that section. The trayed section below the product draw point serves to reject acetylenes and part of the 1,2 butadiene from the net 1,3 butadiene fed to that section.

Zone 3 has sufficient boil-up and reflux (with solvent) and the required number of trays to produce the recovered solvent stream as a bottoms product and an acetylenes rich vapor side stream, while keeping the hydrocarbon concentration of the recovered solvent at specification.

Viewed more abstractly, the subject systems may be regarded as a device to process to separate three classes of components A, B and C in order of relative volatility in a least volatile solvent. For example, in a C4 system, the paraffin-olefin off stream from line 38 may be regarded as component or component class A. The product off line 47 carrying predominantly 1,3 butadiene may be ragarded as product component B. Withdrawal line 56, carrying the acetylene cut may be ragarded as component Class C. Finally, line 58 off the bottom of zone 3 is component class D or predominant recycle solvent.

From this standpoint, zone 1 is set and arranged to limit the quantity of component class C overhead therefrom and component class A in the bottoms thereof. Without limitation, I have found that, when one third of the quantity of component classes A and C permitted in the final product composition are allowed to go into the bottoms and overhead, respectively, of zone 1, then the system may be readily and efficiently be made to work.

Zone 2 is arranged and set to remove component class A, hold B losses to a minimum out the line carrying A and pass classes B and C downwardly.

Zone 4 is arranged and set to remove component class B and pass component class A upwardly and component class C downwardly.

Zone 3 is arranged and set to remove component class C and pass component classes B and A upwardly and component class D (solvent) downwardly.

The attached table gives the inputs and the outputs to and from the system for FIG. 1 (and equivalent lines for the other figures) in pounds per hour and weight percent for line 28 into zone 1 (combined hydrocarbon and solvent recycle feed thereto), line 63 (solvent recycle to the top of zone 2), line 36 (water withdrawal from vessel 35), line 38 (first withdrawal line from the system of paraffin-olefin stream), line 47 (butadiene product withdrawal line to pass to final separation in FIG. 6), line 49 (acetylene withdrawal line from zone 3) and line 58 (solvent recycle from the bottom of zone 3).

These streams are quantified according to a plant producing nominally 200 million pounds per year of butadiene product.

The figures and flows, as may be seen from the component list, are a typical C4 cut being processed in the system and correspond to the C4 cut data given earlier in this specification.

TABLE I(a)

| COMPONENTS | Line 28 | | Line 63 | | Line 36 | | Line 64 | |
|---|---|---|---|---|---|---|---|---|
| | LBS/HR. | WPCT | LBS/HR. | WPCT | LBS/HR. | WPCT | LBS/HR. | WPCT |
| PROPYLENE | 203.24 | 0.103 | 0.00 | 0.000 | 0.00 | 0.000 | 0.00 | 0.000 |
| PROPADIENE | 66.07 | 0.034 | 0.00 | 0.000 | 0.00 | 0.000 | 0.00 | 0.000 |
| PROPYNE | 204.05 | 0.104 | 0.00 | 0.000 | 0.00 | 0.000 | 0.00 | 0.000 |
| ISOBUTANE | 665.75 | 0.339 | 0.00 | 0.000 | 0.00 | 0.000 | 0.00 | 0.000 |
| N—BUTANE | 2610.64 | 1.328 | 0.00 | 0.000 | 0.00 | 0.000 | 0.00 | 0.000 |
| BUTENE-1 | 6853.48 | 3.486 | 0.00 | 0.000 | 0.00 | 0.000 | 0.00 | 0.000 |
| ISOBUTENE | 13055.83 | 6.641 | 0.00 | 0.000 | 0.00 | 0.000 | 0.00 | 0.000 |
| T-BUTENE-2 | 3709.69 | 1.887 | 0.00 | 0.000 | 0.00 | 0.000 | 0.00 | 0.000 |
| C—BUTENE-2 | 3042.34 | 1.547 | 0.00 | 0.000 | 0.00 | 0.000 | 0.00 | 0.000 |
| 1,3 BUTADIENE | 26005.86 | 13.227 | 0.00 | 0.000 | 0.00 | 0.000 | 0.00 | 0.000 |
| 1,2 BUTADIENE | 291.45 | 0.148 | 0.00 | 0.000 | 0.00 | 0.000 | 0.00 | 0.000 |
| BUTYNE-1 | 138.37 | 0.070 | 0.00 | 0.000 | 0.00 | 0.000 | 0.00 | 0.000 |
| VINYLACETYLENE | 470.51 | 0.239 | 3.18 | 10 PPM | 0.00 | 0.000 | 0.00 | 0.000 |
| ACETONITRILE | 126091.13 | 64.133 | 296854.12 | 90.522 | 164.21 | 19.960 | 874.54 | 52.581 |
| WATER | 13200.00 | 6.714 | 31075.99 | 9.476 | 658.48 | 80.039 | 788.69 | 47.419 |
| TOTAL | 196608.41 | 100.000 | 327933.29 | 100.000 | 822.69 | 100.000 | 1663.23 | 100.000 |

TABLE I(b)

| COMPONENTS | Line 38 | | Line 47 | | Line 49 | | Line 61 | |
|---|---|---|---|---|---|---|---|---|
| | LBS/HR. | WPCT | LBS/HR. | WPCT | LBS/HR. | WPCT | LBS/HR. | WPCT |
| PROPYLENE | 203.24 | 0.657 | 0.00 | 0.000 | 0.00 | 0.000 | 0.00 | 0.000 |
| PROPADIENE | 9.38 | 0.030 | 56.69 | 0.222 | 0.00 | 0.000 | 0.00 | 0.000 |
| PROPYNE | 18.27 | 0.059 | 185.78 | 0.726 | 0.00 | 0.000 | 0.00 | 0.000 |
| ISOBUTANE | 665.75 | 2.151 | 0.00 | 0.000 | 0.00 | 0.000 | 0.00 | 0.000 |
| N—BUTANE | 2610.64 | 8.433 | 0.00 | 0.000 | 0.00 | 0.000 | 0.00 | 0.000 |
| BUTENE-1 | 6853.48 | 22.138 | 0.00 | 0.000 | 0.00 | 0.000 | 0.00 | 0.000 |
| ISOBUTENE | 13055.83 | 42.175 | 0.00 | 0.000 | 0.00 | 0.000 | 0.00 | 0.000 |
| T-BUTENE-2 | 3694.32 | 11.933 | 15.37 | 600 PPM | 0.00 | 0.000 | 0.00 | 0.000 |
| C—BUTENE-2 | 2932.93 | 9.474 | 109.41 | 0.428 | 0.00 | 0.000 | 0.00 | 0.000 |
| 1,3 BUTADIENE | 669.76 | 2.163 | 25163.87 | 96.832 | 172.23 | 10.623 | 0.00 | 0.000 |
| 1,2 BUTADIENE | 0.00 | 0.000 | 37.21 | 0.145 | 254.24 | 15.682 | 0.00 | 0.000 |
| BUTYNE-1 | 0.00 | 0.000 | 1.19 | 46.5 PPM | 137.18 | 8.461 | 0.00 | 0.000 |
| VINYLACETYLENE | 0.00 | 0.000 | 0.00 | 0.000 | 468.95 | 28.925 | 4.74 | 10 PPM |
| ACETONITRILE | 225.79 | 0.729 | 0.57 | 22.4 PPM | 483.97 | 29.851 | 422945.25 | 90.552 |
| WATER | 18.02 | 0.058 | 7.73 | 302 PPM | 104.69 | 6.457 | 44275.76 | 9.476 |
| TOTAL | 30957.41 | 100.000 | 25577.82 | 100.000 | 1621.26 | 100.000 | 467225.75 | 100.000 |

WITHDRAWALS FROM ZONES 2, 4 and 3

FIGS. 1–5 and 7 specifically show three withdrawal options in addition to the solvent recycle. That is, specifically shown in these figures are the overhead withdrawal from zone 2, one withdrawal from zone 4 and one withdrawal from zone 3. The solvent recycle is taken from the bottom of zone 3.

In certain conditions, the zone 3 withdrawal intermediate the ends thereof will not be employed. This typically would involve separting two component systems, or at least some of them, wherein there would not be a measurable quantity of impurities present which could be concentrated and withdrawn as a separate stream. This is a relatively unusual circumstance. In such case, then, the withdrawals would be from the top of zone 2 and from zone 4 with the solvent recycle from the bottom of zone 3 and no zone 3 takeoff.

The preferred processes illustrated in the noted FIGS. 1–5, inclusive and 7 (specifically, one takeoff from the top of zone 2, one withdrawal from zone 4, one withdrawal from zone 3 and the zone 3 solvent bottoms recycle) is particularly adapted to butadiene and isoprene recovery where there is no attempt to separate paraffins from olefins. Additionally, this arrangement is applicable to some two component systems which also include minor amounts of impurities which can be concentrated and withdrawn as a separate stream. In such case, it should be noted that the position of withdrawal of the impurity stream with respect to the product streams would depend on the relative volatilities of the components to be separated and the impurities.

In FIGS. 8–10, inclusive, to be described, distillation vessels are shown corresponding to like numbered vessels in FIGS. 1, 2 and 5. In these three vessels, two line withdrawals are shown from zone 4. This arrangement is particularly adapted to butadiene and isoprene recovery where the paraffins are separated from the olefins.

That is, in the three withdrawal showings of FIGS. 1–5 and 7, with respect to a butadiene system, the paraffins and olefins are taken off the top of zone 2, butadiene from zone 4, acetylenes from zone 3 and solvent from the bottom zone 3. In a four withdrawal system as seen in FIGS. 8–10, inclusive, with respect to a butadiene system, paraffins would be taken off zone 2, olefins off the upper zone 4, butadiene off the lower zone 4, acetylenes from zone 3 and solvent recycle from the bottom of zone 3.

It is actually feasible in the butadiene system to take the paraffins and olefins off the top of zone 2 and butadiene and acetylenes together from zone 4. A later separation to obtain the butadiene product would be required. It is also possible to take the paraffins off the top of zone 2, olefins from the upper part of zone 4 and butadiene and acetylenes from the lower portion of zone 4. Again, a later separation would be required to obtain the butadiene product. These options are not preferred.

The two withdrawal showing (from zone 4) of FIGS. 8–10 are equally applicable to the equivalent zone 4's of FIGS. 3 and 4. In such case the single lines 220 and 309 would be replaced by two lines. Solvent separation and recycle would be the same as shown for the single zone 4 line systems for each of the double lines.

With respect to double zone 4 withdrawal systems like those seen in FIGS. 8—10, inclusive, it is also feasible to use such systems with the two component feed streams of FIG. 3 and the like where there are minor amounts of impurities which can be concentrated and withdrawn as two separate streams. As an example of this, in a separation of alcohol and water, low boiling aldehydes could be taken off the top of zone 2, alcohol from the upper portion of zone 4, fusel oil from the lower portion of zone 4, water from zone 3 and solvent recycle from the bottom of zone 3.

Thus it may be seen, where there are two products to be separated, withdrawals would be made from the zones 2 and 4. Where there are three products to be separated, the optimum system involves zone 2, zone 4 and zone 3 withdrawals. With four products to separate, the optimum withdrawals are zone 2, two withdrawals from zone 4 and one from zone 3, as well as the solvent recycle from the bottoms of zone 3 in all cases.

All of the zones and the subject improved thermally coupled extractive distillation system may be provided in a single vessel, but this is not economically attractive.

FIGS. 8–10, INCLUSIVE

FIG. 8 shows a variation on the system of FIG. 1. Specifically, that is, vessel 22 of FIG. 1 may be replaced by vessel 22' of FIG. 8 in the case where the operator wishes to make two drawoffs or withdrawals from zone 4, as previously discussed. That is, in the case of a C4 of C5 cut where it is desired to separate the paraffins and olefins from one another, this system would be used (as an example).

In order to simplify description, all of the parts of vessel 22' identical to like parts of vessel 22 in FIG. 1 are numbered the same, but primed. Additionally, all of the incoming and outgoing lines to vessel 22' which are the same as the incoming and outgoing lines of vessel 22 are numbered the same, but printed. The only difference between the drawings is that lines 41 and 42a of FIG. 1 have been replaced by two sets of lines 701 and 702 and 703 and 704. Line 701 and 702 are the drawoff and return lines from an upper portion of zone 4 which lead to and return from a system exactly that associated with vessel 42 in FIG. 1. Likewise, drawoff line 703 and return line 704, to and from a lower part of zone 4, also lead to a second, but like separation system as seen at 42 or 50 in FIG. 1.

Thus, in the system of FIG. 8, with respect to a C4 extraction system, paraffins would be taken off the top of zone 2 through line 33'. Olefins and solvent would be removed through line 701, a solvent rich fraction being returned in line 702. Line 73 would take off or withdraw butadiene from the lower portion of zone 4, together with solvent, the solvent rich fraction, after separation in the rectifier like tower 42 or 50, being returned in line 704. Acetylene would be removed from zone 3 by line 49, passing to a rectifier tower like tower 50 in FIG. 1 and solvent bottoms taken off through line 58'. Alternatively and preferably with respect to acetylene drawoff in a C4 system, the previously described option would be employed.

FIG. 9 makes the equivalent change for FIG. 2 (substitution of vessel 103' for vessel 103 that vessel 22' did for FIG. 1. Accordingly, FIG. 9 will be but briefly described.

Specifically, all of the parts of vessel 103' and the incoming and outgoing lines therefrom which are identical to that of vessel 103 in FIG. 2 are numbered the same, but primed. The drawoff line 125 and return line 127 to zone 4 in FIG. 2 are replaced by two drawoff and return lines 801–804, inclusive from the upper and lower portions of the zone 4.

In both FIGS. 1 and 2, when the substitute vessels 22' and 103' are, respectively, substituted, all the other parts of the system remain the same. The difference is the provision of two rectifier tower systems with respect to drawoffs 801 and 803 so that solvent rich fractions may be returned at 801 and 804 (or drawoffs 701 and 703 for returns at 702 and 704 in vessel 22').

With respect to FIG. 10, this vessel 399' substitutes for vessel 399 in FIG. 5. All the incoming and outgoing lines that are the same are numbered the same, but primed, as well as the parts of the vessel. The sole change with respect to the FIG. 10 vessel is the replacement of zone 4 drawoff and return lines 425 and 427 with two sets of drawoff and return lines 901–904, inclusive. Again, the drawoff lines 901 and 903 would lead to rectifier towers like tower 426 in FIG. 5 with the return lines 902 and 904 returning solvent rich fractions from the said rectifer towers.

From the foregoing, it will be seen that this invention is one well adapted to attain all of the ends and objects hereinabove set forth together with other advantages which are obvious and which are inherent to the process.

It will be understood that certain process features, steps and sub-combinations thereof are of utility and may be employed without reference to other features, steps and process subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. In a plurality of distillation columns having positioned therewithin a plurality of distillation zones, the process of thermally coupled, extractive distillation comprising the steps of:
   (1) extractively distilling in a first distillation zone a first feed stream containing higher and lower boiling components in the presence of extractive solvent to separate a relatively high volatility overhead vapor stream and a relatively low volatility liquid bottoms stream,
   (2) supplying said overhead stream to the lower portion of a second distillation zone and said bottoms stream to the upper portion of a third distillation zone,
   (3) passing an overhead vapor stream, after dividing same, from said third distillation zone to a lower level of a fourth distillation zone and a lower level of the first distillation zone,
   (4) passing a second feed stream of predominantly extractive solvent to an upper part of the second distillation zone,
   (5) passing a liquid stream from the lower portion of the second distillation zone to an upper level of the first distillation zone and also to an upper level of the fourth distillation zone,
   (6) passing a liquid stream from the lower portion of the fourth distillation zone to an upper portion of the third distillation zone,
   (7) additionally carrying out extractive distillations in said second, third and fourth distillation zones also in the presence of said extractive solvent,
   (8) withdrawing an overhead highest volatility vapor stream from the top of the second distillation zone,
   (9) withdrawing an intermediate, next lower volatility stream, including some extractive solvent, from said fourth distillation zone intermediate the ends thereof,
   (10) withdrawing a lowest volatility liquid bottoms stream, predominantly comprising extractive solvent, from said third distillation zone,
   (11) passing at least a portion of the overhead withdrawal stream from the top of the second distillation zone, as well as a portion of the intermediate withdrawal stream from the fourth distillation zone out of the system,
   (12) condensing said second distillation zone overhead withdrawal vapor stream and recycling at least a portion thereof as reflux to an upper level of the second distillation zone
   (13) heating the lower part of the third distillation zone to aid in accomplishing the distillation of the said four distillation zones, and
   (14) recycling at least a portion of the third distillation zone bottoms withdrawal stream, after cooling thereof, to an upper level of the second distillation zone as the major portion of the second, predominantly extractive solvent feed stream thereto.

2. A process as in claim 1 including also recycling a portion of the third zone bottoms stream to join the first feed stream to the first distillation zone.

3. A process as in claim 1 including separating a portion of the solvent from the fourth distillation zone withdrawal stream and recycling saidseparated solvent to an intermediate level of said fourth distillation zone.

4. A process as in claim 1 including heating the lower part of the third distillation zone sufficiently to substantially entirely accomplish the distillations of the four zones.

5. A process as in claim 1 including adding heat to the lower part of the third distillation zone and at least one of the lower parts of the first and fourth distillation zones in sufficient quantity to substantially entirely accomplish the distillations of the four zones.

6. A process as in claim 1 including compressing the overhead vapor strem from the second zone before condensing same.

7. A process as im claim 6 including compressing the overhed vapor stream from said third distillation zone.

8. A process as in claim 1 wherein the first distillation zone is in a first vessel and the second, third and fourth distillation zones are in a second vessel, with the second distillation zone at the top of the second vessel, the third distillation zone at the bottom of the second vessel and the fourth distillation zone therebetween in the second vessel.

9. A process as in claim 1 wherein the first and second distillation zones are in a first vessel with the second distillation zone positioned above the first distillation zone therein and the third and fourth distillation zones are in a second vessel with the fourth distillation zone above the third distillation zone therein.

10. A process as in claim 1 wherein the first and third distillation zones are in separate vessels and the second and fourth distillation zones are in a third vessel with the second distillation zone above the fourth distillation zone therein.

11. A process as in claim 1 wherein the third distillation zone is in a separate vessel in the first, second and fourth distillation zones are in a second zone, the first and fourth distillation zones being in the lower portion of said second vessel divided from one another and the second distillation zone being in the second vessel thereabove.

12. A process as in claim 1 wherein the first and second distillation zones are in a first vessel with the second zone positioned above the first zone therein and the upper part of the third zone and fourth zone are in a second vessel with the fourth zone above the third zone part therein, the lower part of the third zone being positioned in a third vessel.

13. A process as in claim 1 including compressing the overhead vapor stream from the second zone before condensing same and, additionally, comprising the overhead vapor stream from the third distillation zone before passing same to the lower portions of the first and fourth distillation zones.

14. A process as in claim 1 including withdrawing an intermediate, third lower volatility stream, including some extractive solvent, from the third distillation zone intermediate the ends thereof and passing at least a portion of said intermediate, third lower volatility stream out of the system.

15. A process as in claim 14 including separating a portion of the solvent from the intermediate, third lower volatility stream and recycling the solvent to an intermediate level of said third distillation zone.

16. A process as in claim 1 including withdrawing two intermediate, next lower volatility streams, each including some extractive solvent, from the fourth distillation zone intermediate the ends thereof and passing at least a portion of each thereof out of the system.

17. A process as in claim 16 including separating at least a portion of the solvent from each of the two intermediate, next lower volatility streams from the fourth distillation zone and recycling said separated solvent to an intermediate level of said fourth distillation zone.

18. A process as in claim 1 including the steps of:
taking a liquid draw stream from an intermediate level of the third distillation zone and passing same to a first separating step,
separating said liquid draw stream in said first separating step into a first vapor fraction and a first liquid fraction, the latter predominantly comprising extractive solvent,
passing the said first liquid fraction to a lower portion of the third distillation zone,
recycling at least a portion of said first liquid fraction in the bottoms withdrawal stream of the third distillation zone to an upper level of the second distillation zone as the major portion of the second, predominantly extractive solvent feed stream thereto, and
passing a second vapor stream from said lower portion of the third distillation zone to said first separaing step and recycling at least a portion of the first vapor fraction from said first separating step, after compressing same, to the said intermediate portion of the third distillation zone.

19. A process as in claim 18 including recycling a portion of said first liquid fraction in said bottoms withdrawal stream to join the first feed stream to the first distillation zone.

20. A process as in claim 18 including passing at least a portion of the compressed, first vapor fraction out of the system as a third lower volatility withdrawal stream.

21. A process as in claim 20 including separating the third lower volatility withdrawal stream into relatively light and reltively heavy fractions, recycling the relatively heavy fraction to the first separating step and withdrawing the relatively light fraction from the system as the third lower volatility withdrawal stream.

22. A process as in claim 1 including separating an intermediate liquid withdrawal stream from said third distillation zone into a first vapor fraction and a first liquid fraction in a first separation step,
compressing said first vapor fraction and recycling at least a portion thereof to an intermediate part of the third distillation zone and passing another portion thereof out of the system, after separation of solvent therefrom, as an intermediate, third lower volatility stream,
passing the first liquid fraction to the lower portion of the third distillation zone and therein separating same into a second vapor fraction and a second liquid fraction,
recycling at least a portion of said second liquid fraction to an upper level of the second distillation zone as the major portion of the second, predominantly extractive solvent feed stream thereto, and
recycling at least a portion of the second vapor fraction to said first separation step.

23. A process as in claim 22 including recycling a portion of said second liquid fraction to join the first feed stream to the first distillation zone.

24. A process as in claim 1, including the steps
separating an intermediate liquid withdrawal stream from an intermediate portion of said third distillation zone into a first vapor fraction and a first liquid fraction in a first separation step,
passing at least a portion of said first vapor fraction out of the system as an intermediate third lower volatility withdrawal stream after separation of solvent therefrom,
separating the first liquid fraction into a second vapor fraction and a second liquid fraction in a second separating step,
passing the second liquid fraction to a lower portion of the third distillation zone to produce a liquid bottoms fraction and an overhead vapor fraction therefrom,
recycling at least a portion of said liquid bottoms fraction from said third zone to an upper level of the second distillation zone as the major portion of the second, predominantly extractive solvent feed stream thereto, and
passing at least portions of the second vapor fraction and the first vapor fraction, after compression thereof, to an intermediate portion of the third distillation zone.

25. A process as in claim 24 including recycling a portion of said liquid bottoms fraction to join the first feed stream to the first distillation zone.

* * * * *